(12) United States Patent
de Canniere

(10) Patent No.: US 10,842,626 B2
(45) Date of Patent: Nov. 24, 2020

(54) INTRACARDIAC DEVICE TO CORRECT MITRAL REGURGITATION

(71) Applicant: Didier de Canniere, Brussels (BE)

(72) Inventor: Didier de Canniere, Brussels (BE)

( * ) Notice: Subject to any disclaimer, the term of this patent is extended or adjusted under 35 U.S.C. 154(b) by 135 days.

(21) Appl. No.: 15/974,301

(22) Filed: May 8, 2018

(65) Prior Publication Data

US 2018/0325670 A1    Nov. 15, 2018

Related U.S. Application Data

(63) Continuation-in-part of application No. 14/656,006, filed on Mar. 12, 2015, now abandoned.

(60) Provisional application No. 62/089,339, filed on Dec. 9, 2014.

(51) Int. Cl.
*A61F 2/24* (2006.01)
*A61F 2/958* (2013.01)

(52) U.S. Cl.
CPC ............ *A61F 2/2454* (2013.01); *A61F 2/246* (2013.01); *A61F 2/2442* (2013.01); *A61F 2/2448* (2013.01); *A61F 2/2466* (2013.01); *A61F 2/958* (2013.01); *A61F 2/2457* (2013.01); *A61F 2220/0008* (2013.01); *A61F 2250/0063* (2013.01)

(58) Field of Classification Search
CPC ...... A61F 2/2442; A61F 2/2445; A61F 2/246; A61F 2/2448; A61F 2/2454; A61F 2002/016

See application file for complete search history.

(56) References Cited

U.S. PATENT DOCUMENTS

| | | | |
|---|---|---|---|
| 5,201,742 A | 4/1993 | Hasson | |
| 5,591,170 A | 1/1997 | Spievack et al. | |
| 5,702,421 A | 12/1997 | Schneidt | |
| 6,063,070 A | 5/2000 | Eder | |
| 6,206,907 B1 | 3/2001 | Marino et al. | |
| 6,328,757 B1 | 12/2001 | Matheny | |

(Continued)

FOREIGN PATENT DOCUMENTS

| | | |
|---|---|---|
| EP | 0577400 | 10/1999 |
| EP | 1147743 | 10/2001 |

(Continued)

OTHER PUBLICATIONS

Mike Blaber, Metals, Non-Metals, and Metalloids, http://www.mikeblaber.org/oldwine/chm 1045/notes/Periodic/Metals/Period06.htm, 1996, accessed May 14, 2015.

*Primary Examiner* — Dinah Baria
(74) *Attorney, Agent, or Firm* — Ferguson Case Orr Paterson

(57) ABSTRACT

A device structured to suppress mitral regurgitation by restricting prolapse of a mitral valve leaflet and including a base correspondingly dimensioned to the mitral valve and including a central portion, structured to allow blood flow there through and a peripheral portion or ring connected to the central portion in substantially surrounding relation thereto. An operative position of the base includes the central portion disposed in overlying, movement restricting relation to at least one of the valve leaflets and the ring concurrently anchored adjacent or directly to the native annulus of the mitral valve. The physical characteristics of the base facilitate its movement with and conformance to the mitral valve during diastole and systole cycles of the heart.

14 Claims, 14 Drawing Sheets

(56) References Cited

U.S. PATENT DOCUMENTS

| | | |
|---|---|---|
| 6,425,911 B1 | 7/2002 | Akerfeldt et al. |
| 6,508,828 B1 | 1/2003 | Akerfeldt et al. |
| 6,537,290 B2 | 3/2003 | Adams et al. |
| 6,596,012 B2 | 7/2003 | Akerfeldt et al. |
| 6,682,489 B2 | 1/2004 | Tenerz et al. |
| 6,712,837 B2 | 3/2004 | Åkerfeldt et al. |
| 6,929,655 B2 | 8/2005 | Egnelöv et al. |
| 6,960,220 B2 | 11/2005 | Marino et al. |
| 7,044,916 B2 | 5/2006 | Tenerz et al. |
| 8,147,542 B2 | 4/2012 | Miasano et al. |
| 8,408,214 B2 | 4/2013 | Spenser |
| 8,506,624 B2 | 8/2013 | Vidlund |
| 8,585,755 B2 | 11/2013 | Chau |
| 8,758,393 B2 | 6/2014 | Zentgraf |
| 8,790,394 B2 | 7/2014 | Miller |
| 2002/0100485 A1 | 8/2002 | Stevens et al. |
| 2002/0161378 A1 | 10/2002 | Downing |
| 2003/0120337 A1 | 6/2003 | Van Tassel et al. |
| 2004/0087831 A1 | 5/2004 | Michels et al. |
| 2004/0102804 A1 | 5/2004 | Chin |
| 2004/0106945 A1 | 6/2004 | Thramann et al. |
| 2004/0116897 A1 | 6/2004 | Aboul-Hosn |
| 2004/0138526 A1 | 7/2004 | Guenst |
| 2005/0004668 A1 | 1/2005 | Aklog |
| 2005/0137700 A1 | 6/2005 | Spence et al. |
| 2005/0149108 A1 | 7/2005 | Cox |
| 2006/0074484 A1 | 4/2006 | Huber |
| 2006/0135962 A1 | 6/2006 | Kick et al. |
| 2006/0247672 A1 | 11/2006 | Vidlund et al. |
| 2007/0055206 A1 | 3/2007 | To et al. |
| 2007/0135826 A1 | 6/2007 | Zaver et al. |
| 2007/0162066 A1 | 7/2007 | Lyon |
| 2007/0208215 A1 | 9/2007 | Hjelle |
| 2007/0239108 A1 | 10/2007 | Albrecht et al. |
| 2007/0265643 A1 | 11/2007 | Beane et al. |
| 2008/0033241 A1 | 2/2008 | Peh et al. |
| 2008/0114342 A1 | 5/2008 | Whayne et al. |
| 2008/0275295 A1 | 11/2008 | Gertner |
| 2009/0005800 A1 | 1/2009 | Franer |
| 2009/0105751 A1 | 4/2009 | Zentgraf |
| 2009/0192598 A1 | 7/2009 | Lattouf |
| 2010/0042147 A1 | 2/2010 | Janovsky et al. |
| 2010/0161042 A1 | 6/2010 | Miasano et al. |
| 2010/0161043 A1 | 6/2010 | Miasano et al. |
| 2010/0179574 A1 | 7/2010 | Longoria et al. |
| 2010/0228077 A1 | 9/2010 | Lenker et al. |
| 2010/0274091 A1 | 10/2010 | Rothstein et al. |
| 2011/0029071 A1 | 2/2011 | Zlotnick et al. |
| 2011/0060182 A1 | 3/2011 | Kassab et al. |
| 2011/0166413 A1 | 7/2011 | Alerfness |
| 2011/0190811 A1 | 8/2011 | Shanley |
| 2012/0143209 A1 | 6/2012 | Brecheen et al. |
| 2012/0272452 A1 | 11/2012 | Schultz |
| 2012/0272495 A1 | 11/2012 | Hildebrandt et al. |
| 2012/0272497 A1 | 11/2012 | Smith |
| 2012/0272499 A1 | 11/2012 | Schley et al. |
| 2012/0272523 A1 | 11/2012 | Calla et al. |
| 2012/0272555 A1 | 11/2012 | Heath |
| 2012/0272556 A1 | 11/2012 | Brown |
| 2012/0272595 A1 | 11/2012 | Gallant |
| 2012/0272603 A1 | 11/2012 | Carbines |
| 2012/0272611 A1 | 11/2012 | Tsukimoto et al. |
| 2012/0272624 A1 | 11/2012 | Argeriou et al. |
| 2012/0272632 A1 | 11/2012 | Lans |
| 2012/0272637 A1 | 11/2012 | Holland et al. |
| 2012/0272652 A1 | 11/2012 | Nicholls et al. |
| 2012/0272653 A1 | 11/2012 | Merrill et al. |
| 2012/0272660 A1 | 11/2012 | Garrett |
| 2012/0272661 A1 | 11/2012 | Milburn |
| 2012/0272662 A1 | 11/2012 | Milburn |
| 2012/0272667 A1 | 11/2012 | Ferraro et al. |
| 2012/0272670 A1 | 11/2012 | Choi et al. |
| 2012/0272705 A1 | 11/2012 | Hirane |
| 2012/0272738 A1 | 11/2012 | Klessel et al. |
| 2012/0272741 A1 | 11/2012 | Xiao et al. |
| 2012/0272768 A1 | 11/2012 | Schmidt et al. |
| 2012/0272780 A1 | 11/2012 | Schimings et al. |
| 2012/0272815 A1 | 11/2012 | Lingel et al. |
| 2012/0272817 A1 | 11/2012 | Lindh, Sr. et al. |
| 2012/0272841 A1 | 11/2012 | Heymanns et al. |
| 2012/0272843 A1 | 11/2012 | Graff |
| 2012/0272845 A1 | 11/2012 | Loiret-Bernal et al. |
| 2012/0272846 A1 | 11/2012 | Fleischer et al. |
| 2012/0272876 A1 | 11/2012 | Bergeron et al. |
| 2012/0272893 A1 | 11/2012 | Lauerhaas et al. |
| 2012/0272968 A1 | 11/2012 | Kirschner |
| 2012/0272996 A1 | 11/2012 | Jimenez et al. |
| 2012/0273014 A1 | 11/2012 | Tadayon |
| 2012/0273064 A1 | 11/2012 | Ismert et al. |
| 2012/0273078 A1 | 11/2012 | Hawwa et al. |
| 2012/0273079 A1 | 11/2012 | Guclucan |
| 2012/0273141 A1 | 11/2012 | Miller et al. |
| 2012/0273142 A1 | 11/2012 | Miller et al. |
| 2012/0273143 A1 | 11/2012 | Fillmore et al. |
| 2012/0273161 A1 | 11/2012 | Raver |
| 2012/0273174 A1 | 11/2012 | Barnes |
| 2012/0273178 A1 | 11/2012 | Wanni et al. |
| 2012/0273209 A1 | 11/2012 | Austin et al. |
| 2012/0273210 A1 | 11/2012 | Arizmendi, Jr. et al. |
| 2012/0273214 A1 | 11/2012 | Donald et al. |
| 2012/0273219 A1 | 11/2012 | Hoffman et al. |
| 2012/0273220 A1 | 11/2012 | Ezekiel et al. |
| 2012/0273228 A1 | 11/2012 | Allouche |
| 2012/0273230 A1 | 11/2012 | Patterson et al. |
| 2012/0273231 A1 | 11/2012 | Whiddon |
| 2012/0273232 A1 | 11/2012 | O'Blenes |
| 2012/0273328 A1 | 11/2012 | Sejourne |
| 2012/0273358 A1 | 11/2012 | Larnoy et al. |
| 2012/0273389 A1 | 11/2012 | Aziz et al. |
| 2012/0273399 A1 | 11/2012 | Daboub et al. |
| 2012/0273438 A1 | 11/2012 | Nordin et al. |
| 2012/0273439 A1 | 11/2012 | Beavers et al. |
| 2012/0273458 A1 | 11/2012 | Bret et al. |
| 2012/0273467 A1 | 11/2012 | Baxter et al. |
| 2012/0273470 A1 | 11/2012 | Zediker et al. |
| 2012/0273518 A1 | 11/2012 | Greer, Jr. |
| 2012/0273555 A1 | 11/2012 | Flak et al. |
| 2012/0273580 A1 | 11/2012 | Warren et al. |
| 2012/0273641 A1 | 11/2012 | Gorman et al. |
| 2012/0273647 A1 | 11/2012 | Moruzzi |
| 2012/0273680 A1 | 11/2012 | Furry |
| 2012/0273843 A1 | 11/2012 | Kim |
| 2012/0273860 A1 | 11/2012 | Chen et al. |
| 2012/0273880 A1 | 11/2012 | Teng et al. |
| 2012/0273902 A1 | 11/2012 | Lin et al. |
| 2012/0273955 A1 | 11/2012 | Or-Bach et al. |
| 2012/0273987 A1 | 11/2012 | Belcher et al. |
| 2012/0273989 A1 | 11/2012 | Graf |
| 2012/0273993 A1 | 11/2012 | Shoseyov et al. |
| 2012/0274001 A1 | 11/2012 | Prabhu |
| 2012/0274020 A1 | 11/2012 | Daboub |
| 2012/0274061 A1 | 11/2012 | Wilkinson |
| 2012/0274065 A1 | 11/2012 | Knapp |
| 2012/0274068 A1 | 11/2012 | Hanback |
| 2012/0274076 A1 | 11/2012 | Kelaiditis et al. |
| 2012/0274145 A1 | 11/2012 | Taddeo |
| 2012/0274198 A1 | 11/2012 | Jenek |
| 2012/0274202 A1 | 11/2012 | Komatsu |
| 2012/0274212 A1 | 11/2012 | Yu et al. |
| 2012/0274256 A1 | 11/2012 | O'Rourke |
| 2012/0274266 A1 | 11/2012 | Yip |
| 2012/0274279 A1 | 11/2012 | Banos et al. |
| 2012/0274280 A1 | 11/2012 | Yip et al. |
| 2012/0274281 A1 | 11/2012 | Kim |
| 2012/0274288 A1 | 11/2012 | Wegener |
| 2012/0274332 A1 | 11/2012 | Sinha et al. |
| 2012/0274391 A1 | 11/2012 | Kim |
| 2012/0274395 A1 | 11/2012 | Deam |
| 2012/0274440 A1 | 11/2012 | Meadows et al. |
| 2012/0274470 A1 | 11/2012 | Sandvick |
| 2012/0274477 A1 | 11/2012 | Prammer |
| 2012/0274769 A1 | 11/2012 | Lee |
| 2012/0274770 A1 | 11/2012 | Lee |
| 2012/0274772 A1 | 11/2012 | Fosburgh et al. |

(56) References Cited

U.S. PATENT DOCUMENTS

| | | |
|---|---|---|
| 2012/0274870 A1 | 11/2012 | Liu |
| 2012/0274937 A1 | 11/2012 | Hays et al. |
| 2012/0274962 A1 | 11/2012 | Thomas et al. |
| 2012/0275056 A1 | 11/2012 | McGuire, Jr. |
| 2012/0275057 A1 | 11/2012 | McGuire, Jr. |
| 2012/0275085 A1 | 11/2012 | Wilson et al. |
| 2012/0275128 A1 | 11/2012 | Takada et al. |
| 2012/0275140 A1 | 11/2012 | Feinbloom et al. |
| 2012/0275236 A1 | 11/2012 | Hess et al. |
| 2012/0275244 A1 | 11/2012 | Do |
| 2012/0275247 A1 | 11/2012 | Hwang et al. |
| 2012/0275248 A1 | 11/2012 | Won |
| 2012/0275249 A1 | 11/2012 | Yang et al. |
| 2012/0275298 A1 | 11/2012 | Bryant et al. |
| 2012/0275299 A1 | 11/2012 | Taylor et al. |
| 2012/0275338 A1 | 11/2012 | Filsfils et al. |
| 2012/0275356 A1 | 11/2012 | Aharony et al. |
| 2012/0275670 A1 | 11/2012 | Joglekar |
| 2012/0275754 A1 | 11/2012 | Krampotich et al. |
| 2012/0275841 A1 | 11/2012 | Jimenez et al. |
| 2012/0275843 A1 | 11/2012 | Jimenez et al. |
| 2012/0275845 A1 | 11/2012 | Etling |
| 2012/0275860 A1 | 11/2012 | Exline |
| 2012/0275861 A1 | 11/2012 | Myslowski et al. |
| 2012/0275862 A1 | 11/2012 | Vitale |
| 2012/0275881 A1 | 11/2012 | Mueller |
| 2012/0275913 A1 | 11/2012 | Robertson, Jr. et al. |
| 2012/0275924 A1 | 11/2012 | Perkinson |
| 2012/0275927 A1 | 11/2012 | Rhim |
| 2012/0275970 A1 | 11/2012 | Nash et al. |
| 2012/0275999 A1 | 11/2012 | Bell et al. |
| 2012/0276005 A1 | 11/2012 | Yang et al. |
| 2012/0276008 A1 | 11/2012 | Walkenhorst et al. |
| 2012/0276009 A1 | 11/2012 | Pfeifer et al. |
| 2012/0276011 A1 | 11/2012 | Kupussamy et al. |
| 2012/0276021 A1 | 11/2012 | Kumar et al. |
| 2012/0276025 A1 | 11/2012 | Florence et al. |
| 2012/0276041 A1 | 11/2012 | Salamone et al. |
| 2012/0276053 A1 | 11/2012 | Kirn |
| 2012/0276061 A1 | 11/2012 | Grazia et al. |
| 2012/0276062 A1 | 11/2012 | Kellar et al. |
| 2012/0276064 A1 | 11/2012 | Blau et al. |
| 2012/0276067 A1 | 11/2012 | Westenfelder |
| 2012/0276068 A1 | 11/2012 | Sabaawy |
| 2012/0276069 A1 | 11/2012 | Karperien et al. |
| 2012/0276071 A1 | 11/2012 | Fraser, Jr. |
| 2012/0276073 A1 | 11/2012 | Schachner et al. |
| 2012/0276074 A1 | 11/2012 | Scharenberg et al. |
| 2012/0276080 A1 | 11/2012 | Kinoshita et al. |
| 2012/0276084 A1 | 11/2012 | Schaumberg et al. |
| 2012/0276087 A1 | 11/2012 | Schafer et al. |
| 2012/0276088 A1 | 11/2012 | El-Deiry et al. |
| 2012/0276089 A1 | 11/2012 | Lee et al. |
| 2012/0276101 A1 | 11/2012 | Kwak et al. |
| 2012/0276103 A1 | 11/2012 | Karperien et al. |
| 2012/0276104 A1 | 11/2012 | Woisetschlager |
| 2012/0276110 A1 | 11/2012 | Simard |
| 2012/0276111 A1 | 11/2012 | Hafezi-Moghadam |
| 2012/0276126 A1 | 11/2012 | Varadhachary et al. |
| 2012/0276130 A1 | 11/2012 | Margarit Y Ros et al. |
| 2012/0276139 A1 | 11/2012 | Moormann et al. |
| 2012/0276143 A1 | 11/2012 | O'Mahony et al. |
| 2012/0276144 A1 | 11/2012 | Kernodle et al. |
| 2012/0276149 A1 | 11/2012 | Littman et al. |
| 2012/0276150 A1 | 11/2012 | Lauritzen et al. |
| 2012/0276151 A1 | 11/2012 | Lewis et al. |
| 2012/0276152 A1 | 11/2012 | Hossainy et al. |
| 2012/0276161 A1 | 11/2012 | Gravagna et al. |
| 2012/0276164 A1 | 11/2012 | Tuominen et al. |
| 2012/0276169 A1 | 11/2012 | Kang et al. |
| 2012/0276173 A1 | 11/2012 | Marcum et al. |
| 2012/0276182 A1 | 11/2012 | Baker, Jr. et al. |
| 2012/0276185 A1 | 11/2012 | Hossainy et al. |
| 2012/0276188 A1 | 11/2012 | Barrows |
| 2012/0276189 A1 | 11/2012 | Johnson |
| 2012/0276193 A1 | 11/2012 | Graversen et al. |
| 2012/0276201 A1 | 11/2012 | Trachtman |
| 2012/0276202 A1 | 11/2012 | Selim et al. |
| 2012/0276203 A1 | 11/2012 | Selim et al. |
| 2012/0276204 A1 | 11/2012 | Remington et al. |
| 2012/0276213 A1 | 11/2012 | Chen |
| 2012/0276218 A1 | 11/2012 | Jung et al. |
| 2012/0276232 A1 | 11/2012 | Marczyk et al. |
| 2012/0276237 A1 | 11/2012 | Heymanns et al. |
| 2012/0276278 A1 | 11/2012 | Qiu et al. |
| 2012/0276286 A1 | 11/2012 | Vijayakumar |
| 2012/0276296 A1 | 11/2012 | Fieberg et al. |
| 2012/0276297 A1 | 11/2012 | Cypcar et al. |
| 2012/0276304 A1 | 11/2012 | Derrien |
| 2012/0276330 A1 | 11/2012 | Durney et al. |
| 2012/0276365 A1 | 11/2012 | Petuskey et al. |
| 2012/0276375 A1 | 11/2012 | Colgan et al. |
| 2012/0276381 A1 | 11/2012 | Cypcar |
| 2012/0276427 A1 | 11/2012 | Kim |
| 2012/0276463 A1 | 11/2012 | Grannell et al. |
| 2012/0276465 A1 | 11/2012 | Paganelli |
| 2012/0276469 A1 | 11/2012 | Shizuku |
| 2012/0276509 A1 | 11/2012 | Iannotti et al. |
| 2012/0276518 A1 | 11/2012 | Gillis |
| 2012/0276522 A1 | 11/2012 | Huang et al. |
| 2012/0276528 A1 | 11/2012 | Cargill et al. |
| 2012/0276529 A1 | 11/2012 | Galisson et al. |
| 2012/0276537 A1 | 11/2012 | Kühn et al. |
| 2012/0276552 A1 | 11/2012 | Lu |
| 2012/0276553 A1 | 11/2012 | Gronthos et al. |
| 2012/0276554 A1 | 11/2012 | Gutteridge et al. |
| 2012/0276555 A1 | 11/2012 | Kuhn et al. |
| 2012/0276558 A1 | 11/2012 | Soper et al. |
| 2012/0276572 A1 | 11/2012 | Shekdar et al. |
| 2012/0276581 A1 | 11/2012 | Arav et al. |
| 2012/0276588 A1 | 11/2012 | Hallen-Adams et al. |
| 2012/0276591 A1 | 11/2012 | Kneissel et al. |
| 2012/0276618 A1 | 11/2012 | Dayton et al. |
| 2012/0276626 A1 | 11/2012 | Shogbon et al. |
| 2012/0276627 A1 | 11/2012 | Kelnar et al. |
| 2012/0276628 A1 | 11/2012 | Khan et al. |
| 2012/0276632 A1 | 11/2012 | Strunk et al. |
| 2012/0276679 A1 | 11/2012 | Wu |
| 2012/0276694 A1 | 11/2012 | Koezuka et al. |
| 2012/0276754 A1 | 11/2012 | Cordingley et al. |
| 2012/0276887 A1 | 11/2012 | Romine et al. |
| 2012/0276928 A1 | 11/2012 | Shutter |
| 2012/0277006 A1 | 11/2012 | Kim |
| 2012/0277008 A1 | 11/2012 | Kitchen et al. |
| 2012/0277051 A1 | 11/2012 | Cooper et al. |
| 2012/0277073 A1 | 11/2012 | Bartsch |
| 2012/0277093 A1 | 11/2012 | Andrew et al. |
| 2012/0277110 A1 | 11/2012 | Andre et al. |
| 2012/0277111 A1 | 11/2012 | Crabtree et al. |
| 2012/0277112 A1 | 11/2012 | Linn et al. |
| 2012/0277118 A1 | 11/2012 | Bhati et al. |
| 2012/0277120 A1 | 11/2012 | Serber et al. |
| 2012/0277144 A1 | 11/2012 | Duckers |
| 2012/0277152 A1 | 11/2012 | Ringeisen et al. |
| 2012/0277155 A1 | 11/2012 | VanAntwerp et al. |
| 2012/0277156 A1 | 11/2012 | Gross et al. |
| 2012/0277157 A1 | 11/2012 | Hillman |
| 2012/0277161 A1 | 11/2012 | Agrez et al. |
| 2012/0277162 A1 | 11/2012 | Krasnoperov et al. |
| 2012/0277173 A1 | 11/2012 | Eidenberger |
| 2012/0277179 A1 | 11/2012 | Bhargava |
| 2012/0277195 A1 | 11/2012 | Banov et al. |
| 2012/0277203 A1 | 11/2012 | Lasley et al. |
| 2012/0277204 A1 | 11/2012 | Taniguchi et al. |
| 2012/0277205 A1 | 11/2012 | Badorc et al. |
| 2012/0277210 A1 | 11/2012 | Catron et al. |
| 2012/0277215 A1 | 11/2012 | Ksander et al. |
| 2012/0277228 A1 | 11/2012 | Sutton et al. |
| 2012/0277229 A1 | 11/2012 | Bearss et al. |
| 2012/0277251 A1 | 11/2012 | Palladino et al. |
| 2012/0277265 A1 | 11/2012 | Deraeve et al. |
| 2012/0277269 A1 | 11/2012 | Reilly |
| 2012/0277271 A1 | 11/2012 | Nadeson et al. |
| 2012/0277277 A1 | 11/2012 | Wallace et al. |

(56) References Cited

U.S. PATENT DOCUMENTS

| | | |
|---|---|---|
| 2012/0277279 A1 | 11/2012 | Barnett et al. |
| 2012/0277282 A1 | 11/2012 | Gotthardt et al. |
| 2012/0277288 A1 | 11/2012 | Drumm et al. |
| 2012/0277307 A1 | 11/2012 | Waddell |
| 2012/0277309 A1 | 11/2012 | Severa et al. |
| 2012/0277312 A1 | 11/2012 | Mink et al. |
| 2012/0277316 A1 | 11/2012 | Tillman et al. |
| 2012/0277319 A1 | 11/2012 | Steigerwald et al. |
| 2012/0277324 A1 | 11/2012 | Burk et al. |
| 2012/0277364 A1 | 11/2012 | Lolli et al. |
| 2012/0277376 A1 | 11/2012 | Baker, Jr. et al. |
| 2012/0277382 A1 | 11/2012 | Booth et al. |
| 2012/0277412 A1 | 11/2012 | Furusako et al. |
| 2012/0277430 A1 | 11/2012 | Taniguchi et al. |
| 2012/0277431 A1 | 11/2012 | Taniguchi et al. |
| 2012/0277451 A1 | 11/2012 | Ochiai |
| 2012/0277453 A1 | 11/2012 | Franklin et al. |
| 2012/0277517 A1 | 11/2012 | Ivkov et al. |
| 2012/0277521 A1 | 11/2012 | Chamberlin |
| 2012/0277522 A1 | 11/2012 | Shalon et al. |
| 2012/0277523 A1 | 11/2012 | Shalon et al. |
| 2012/0277537 A1 | 11/2012 | Kucklick et al. |
| 2012/0277544 A1 | 11/2012 | Fernandes et al. |
| 2012/0277546 A1 | 11/2012 | Soykan et al. |
| 2012/0277567 A1 | 11/2012 | Harley et al. |
| 2012/0277572 A1 | 11/2012 | Hubbard |
| 2012/0277574 A1 | 11/2012 | Panescu |
| 2012/0277576 A1 | 11/2012 | Lui |
| 2012/0277578 A1 | 11/2012 | Gunday et al. |
| 2012/0277582 A1 | 11/2012 | Mafi |
| 2012/0277584 A1 | 11/2012 | Tanaka et al. |
| 2012/0277592 A1 | 11/2012 | Zelenka et al. |
| 2012/0277599 A1 | 11/2012 | Greenhut |
| 2012/0277600 A1 | 11/2012 | Greenhut |
| 2012/0277618 A1 | 11/2012 | Giftakis et al. |
| 2012/0277621 A1 | 11/2012 | Gerber et al. |
| 2012/0277624 A1 | 11/2012 | Cucin |
| 2012/0277626 A1 | 11/2012 | Burbank et al. |
| 2012/0277638 A1 | 11/2012 | Skelton et al. |
| 2012/0277639 A1 | 11/2012 | Pollock et al. |
| 2012/0277642 A1 | 11/2012 | Smith et al. |
| 2012/0277668 A1 | 11/2012 | Chawla |
| 2012/0277671 A1 | 11/2012 | Fuentes |
| 2012/0277672 A1 | 11/2012 | Pepper et al. |
| 2012/0277674 A1 | 11/2012 | Clark, III et al. |
| 2012/0277693 A1 | 11/2012 | Bailey |
| 2012/0277716 A1 | 11/2012 | Ali et al. |
| 2012/0277718 A1 | 11/2012 | Campbell et al. |
| 2012/0277720 A1 | 11/2012 | Humes et al. |
| 2012/0277725 A1 | 11/2012 | Kassab et al. |
| 2012/0277729 A1 | 11/2012 | Melsheimer |
| 2012/0277730 A1 | 11/2012 | Salahieh et al. |
| 2012/0277736 A1 | 11/2012 | Francischelli |
| 2012/0277740 A1 | 11/2012 | Warnking et al. |
| 2012/0277741 A1 | 11/2012 | Davalos et al. |
| 2012/0277743 A1 | 11/2012 | Vallittu |
| 2012/0277746 A1 | 11/2012 | Morgan et al. |
| 2012/0277749 A1 | 11/2012 | Mootien et al. |
| 2012/0277752 A1 | 11/2012 | Wasielewski |
| 2012/0277753 A1 | 11/2012 | Linderman et al. |
| 2012/0277756 A1 | 11/2012 | Ray et al. |
| 2012/0277766 A1 | 11/2012 | Ferree |
| 2012/0277770 A1 | 11/2012 | Fenton et al. |
| 2012/0277771 A1 | 11/2012 | Vaz et al. |
| 2012/0277772 A1 | 11/2012 | Aben et al. |
| 2012/0277773 A1 | 11/2012 | Sargeant et al. |
| 2012/0277774 A1 | 11/2012 | Guo |
| 2012/0277776 A1 | 11/2012 | Kraemer et al. |
| 2012/0277781 A1 | 11/2012 | Gertner |
| 2012/0277784 A1 | 11/2012 | Berez et al. |
| 2012/0277785 A1 | 11/2012 | Aggerholm et al. |
| 2012/0277786 A1 | 11/2012 | Mohl |
| 2012/0277791 A1 | 11/2012 | Abo-Auda et al. |
| 2012/0277792 A1 | 11/2012 | Teeslink et al. |
| 2012/0277793 A1 | 11/2012 | Marczyk et al. |
| 2012/0277798 A1 | 11/2012 | Benson et al. |
| 2012/0277800 A1 | 11/2012 | Jackson |
| 2012/0277807 A1 | 11/2012 | Myung et al. |
| 2012/0277811 A1 | 11/2012 | Lauchner et al. |
| 2012/0277812 A1 | 11/2012 | Kraus |
| 2012/0277814 A1 | 11/2012 | Schuler |
| 2012/0277820 A1 | 11/2012 | Wu et al. |
| 2012/0277823 A1 | 11/2012 | Gerber et al. |
| 2012/0277825 A1 | 11/2012 | Mawson et al. |
| 2012/0277833 A1 | 11/2012 | Gerber et al. |
| 2012/0277835 A1 | 11/2012 | Della Santina et al. |
| 2012/0277837 A1 | 11/2012 | Schuler |
| 2012/0277843 A1 | 11/2012 | Weber et al. |
| 2012/0277845 A1 | 11/2012 | Bowe |
| 2012/0277846 A1 | 11/2012 | Schreck et al. |
| 2012/0277852 A1 | 11/2012 | Shukla et al. |
| 2012/0277853 A1 | 11/2012 | Rothstein |
| 2012/0277854 A1 | 11/2012 | Ryan |
| 2012/0277855 A1 | 11/2012 | Lashinski et al. |
| 2012/0277856 A1 | 11/2012 | Spenser et al. |
| 2012/0277862 A1 | 11/2012 | Tornier et al. |
| 2012/0277864 A1 | 11/2012 | Brodke et al. |
| 2012/0277865 A1 | 11/2012 | Trieu et al. |
| 2012/0277867 A1 | 11/2012 | Kana et al. |
| 2012/0277872 A1 | 11/2012 | Kana et al. |
| 2012/0277873 A1 | 11/2012 | Kana et al. |
| 2012/0277879 A1 | 11/2012 | Ripamonti |
| 2012/0277880 A1 | 11/2012 | Winslow et al. |
| 2012/0277882 A1 | 11/2012 | Huang et al. |
| 2012/0277896 A1 | 11/2012 | Uekita et al. |
| 2012/0277903 A1 | 11/2012 | Schaefer |
| 2012/0277939 A1 | 11/2012 | Kumar |
| 2012/0277940 A1 | 11/2012 | Kumar et al. |
| 2012/0277949 A1 | 11/2012 | Ghimire et al. |
| 2012/0277979 A1 | 11/2012 | Kato et al. |
| 2012/0277998 A1 | 11/2012 | Bevilacqua et al. |
| 2012/0277999 A1 | 11/2012 | Somogyi et al. |
| 2012/0278032 A1 | 11/2012 | Chen |
| 2012/0278098 A1 | 11/2012 | Vovan et al. |
| 2012/0278099 A1 | 11/2012 | Kelly et al. |
| 2012/0278123 A1 | 11/2012 | Houle |
| 2012/0278144 A1 | 11/2012 | Popilock et al. |
| 2012/0278195 A1 | 11/2012 | Joseph |
| 2012/0278200 A1 | 11/2012 | van Coppenolle et al. |
| 2012/0278236 A1 | 11/2012 | Jain et al. |
| 2012/0278242 A1 | 11/2012 | Griffith |
| 2012/0278411 A1 | 11/2012 | Lavine |
| 2012/0278439 A1 | 11/2012 | Ahiska et al. |
| 2012/0278454 A1 | 11/2012 | Stewart et al. |
| 2012/0278484 A1 | 11/2012 | Westphal |
| 2012/0278520 A1 | 11/2012 | Barrenscheen et al. |
| 2012/0278554 A1 | 11/2012 | Eilert |
| 2012/0278592 A1 | 11/2012 | Tran |
| 2012/0278597 A1 | 11/2012 | De Atley et al. |
| 2012/0278654 A1 | 11/2012 | Shen et al. |
| 2012/0278657 A1 | 11/2012 | Baker et al. |
| 2012/0278676 A1 | 11/2012 | Teraura |
| 2012/0278684 A1 | 11/2012 | Eldredge et al. |
| 2012/0278689 A1 | 11/2012 | Tamo et al. |
| 2012/0278760 A1 | 11/2012 | Cerny et al. |
| 2012/0278771 A1 | 11/2012 | Ren |
| 2012/0278799 A1 | 11/2012 | Starks et al. |
| 2012/0278865 A1 | 11/2012 | Sawdy |
| 2012/0278913 A1 | 11/2012 | Fraser |
| 2012/0278947 A1 | 11/2012 | Guo et al. |
| 2012/0278957 A1 | 11/2012 | Phan et al. |
| 2012/0283758 A1 | 11/2012 | Miller |
| 2013/0041395 A1 | 2/2013 | De Canniere |
| 2013/0066275 A1 | 3/2013 | De Canniere |
| 2014/0276922 A1 | 9/2014 | McLain |

FOREIGN PATENT DOCUMENTS

| | | |
|---|---|---|
| EP | 1169968 | 1/2002 |
| EP | 1222896 | 7/2002 |
| EP | 1266626 | 12/2002 |
| EP | 1269919 | 1/2003 |
| EP | 1254634 | 7/2003 |
| EP | 1244725 | 7/2005 |

(56) References Cited

FOREIGN PATENT DOCUMENTS

| | | |
|---|---|---|
| EP | 1773239 | 3/2010 |
| WO | WO2012040865 | 4/2012 |
| WO | WO2012016398 | 9/2012 |
| WO | WO2013/023016 | 2/2013 |
| WO | WO2013036742 | 3/2013 |
| WO | WO2015081053 | 6/2015 |
| WO | WO2016/094490 | 6/2016 |

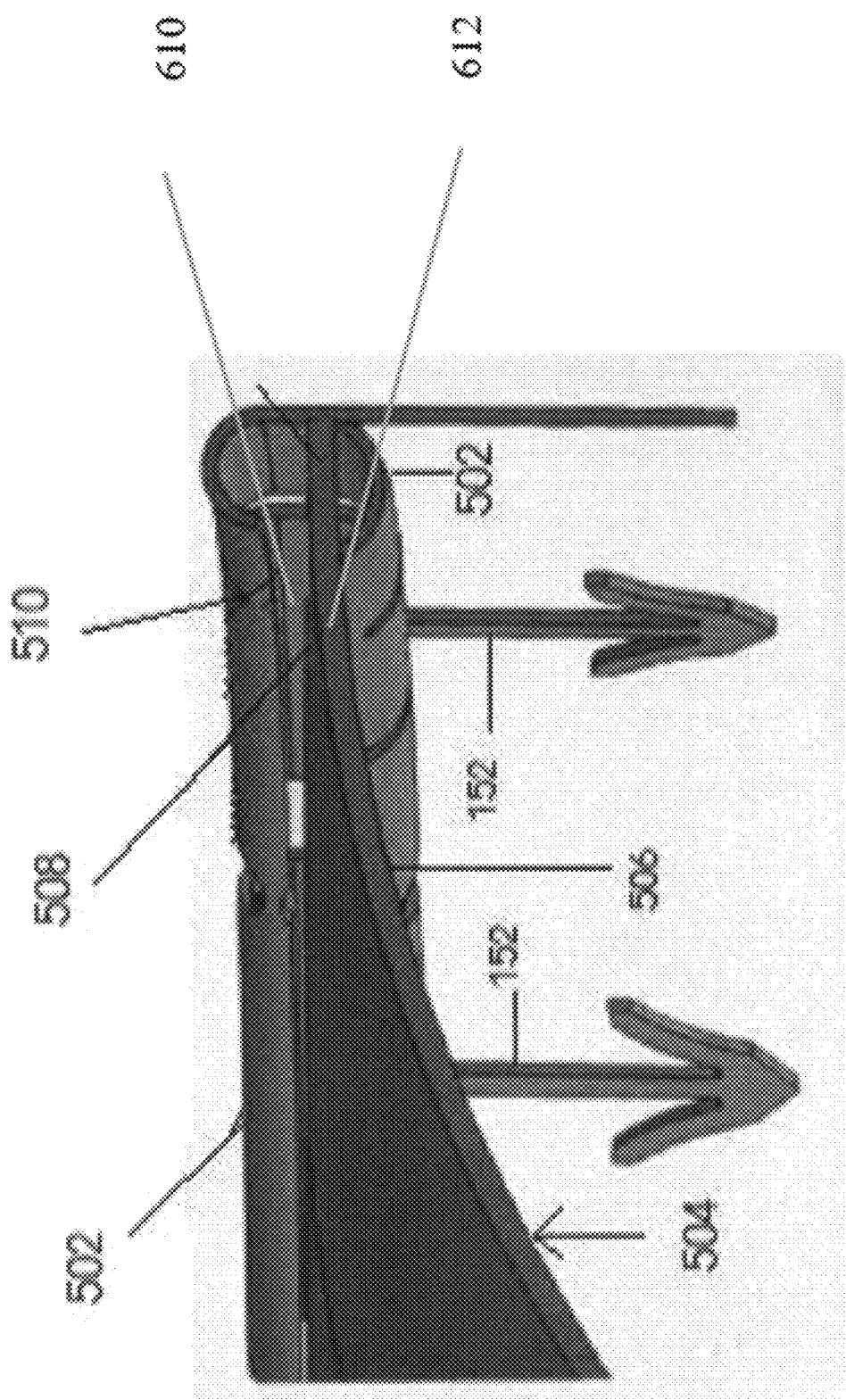

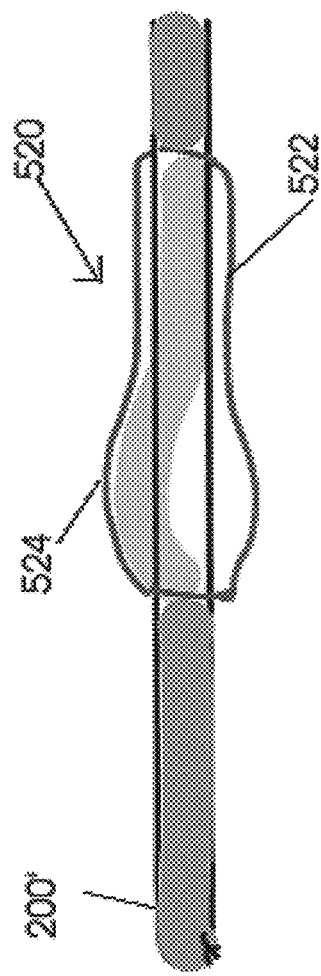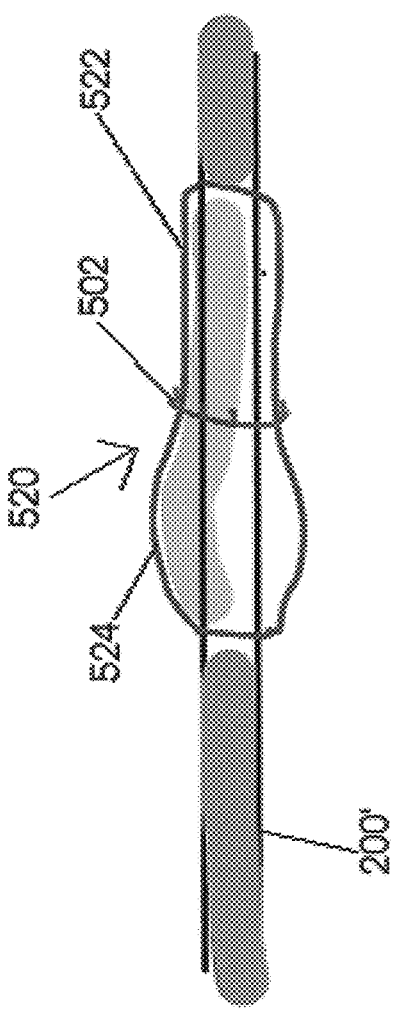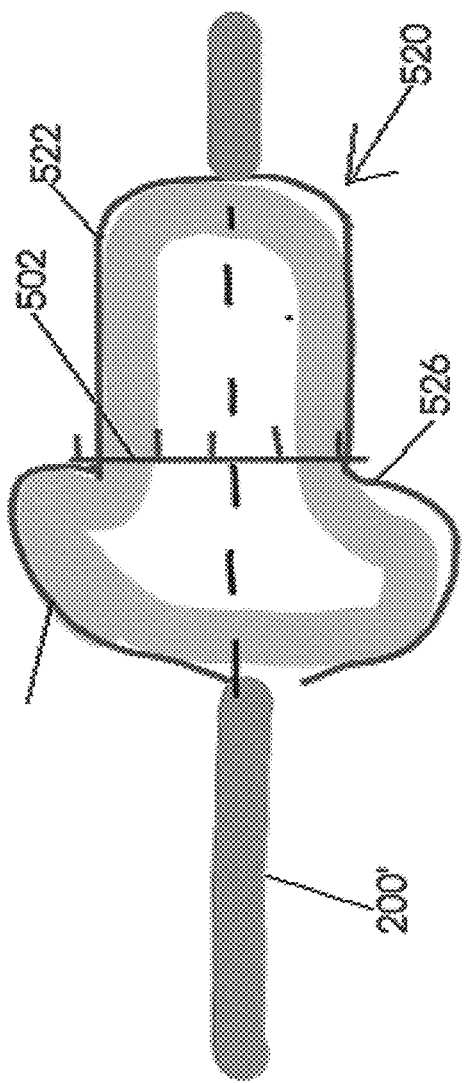

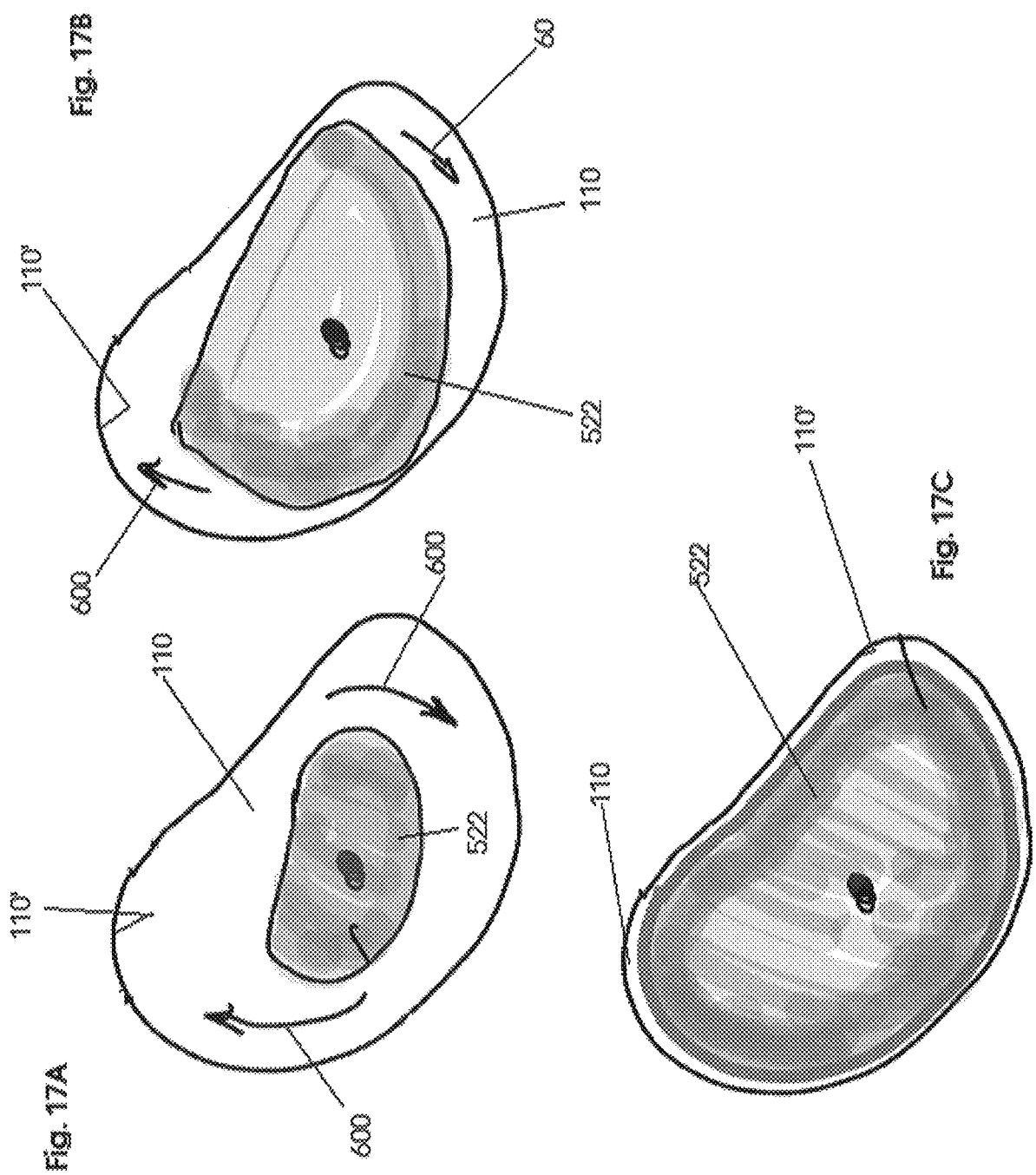

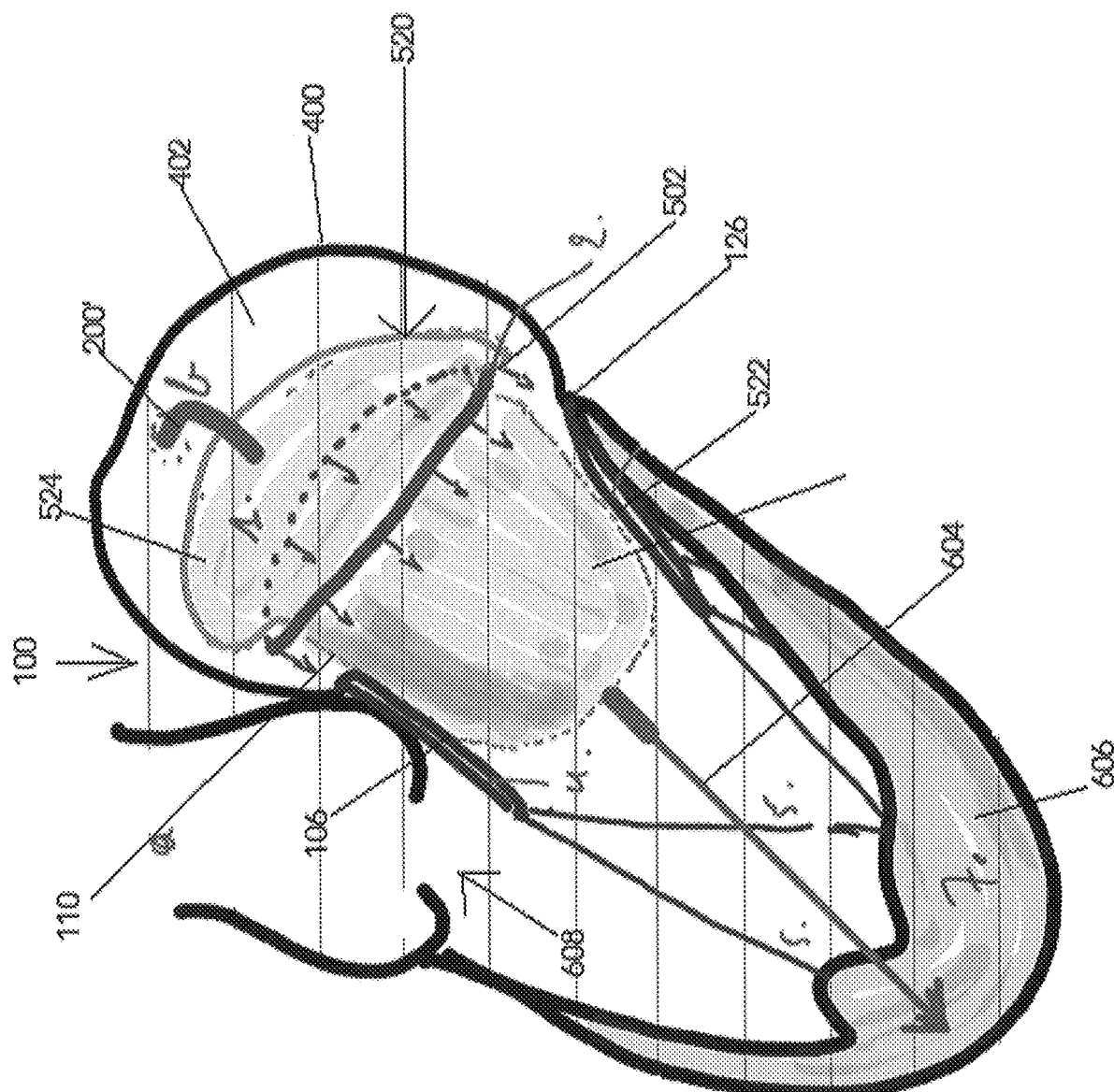

INTRACARDIAC DEVICE TO CORRECT MITRAL REGURGITATION

CLAIM OF PRIORITY

The present application is a continuation-in-part of U.S. patent application Ser. No. 14/656,006, filed on Mar. 12, 2015, which claims priority under 35 U.S.C. Section 119(e) to a provisional patent application having Ser. No. 62/089,339 and a filing date of Dec. 9, 2014, and which is incorporated herein by reference.

BACKGROUND OF THE INVENTION

Field of the Invention

The invention relates to a device, for use in the field of minimally invasive surgery or invasive cardiology, capable of introduction through a minimal incision, a port-access in the wall of the left atrium or via a trans-septal, catheter-based, approach to the mitral valve from a peripheral vein such as the femoral or jugular. The device is disposed that and structured to prevent a flail mitral leaflet from flipping back into the left atrium ("prolapsing") in order to remodel the shape and movement of the mitral structures in such a way to improve the coaptation of the mitral leaflets and hence decrease or suppress the mitral regurgitation flow.

Description of the Related Art

The mitral valve is located between the left atrium (LA) and the left ventricle (LV). It is due to open fully to not oppose resistance to the blood stream progressing from the LA to the LV during the diastole (i.e. the ventricular relaxation phase) and to close fully during the systole (the ventricular ejection phase) so as to prevent the blood from flowing back into the left atrium and to the pulmonary venous circulation. The role of the mitral valve is therefore to ensure antegrade progression of the blood through the left cardiac chambers. It works in synchrony with the three other heart valves that are ensuring the same function between the right atrium (RA) and the right ventricle (RV) i.e. the tricuspid valve, between the right ventricle and the pulmonary artery (PA) i.e. the pulmonic valve and downstream to the mitral valve, between the left ventricle and the aorta i.e. the aortic valve at the junction between the left ventricle and the aorta, the latter to opening during the ventricular systoles and closing during diastole. From a mechanical standpoint the mitral valve has to face high gradients of pressure during the ventricular contraction to hold up against a pressure head of about 100 mm of mercury (Hg) or more. It is recognized that the peak pressure in the LV is generally equal to or greater than 110 mmHg and the one in the atrium around 10 mmHg. This strain is absorbed mostly by the coaptation of the two mitral leaflets when closed, comprising the valve leaflets closing with each other with a contact height around 10 mm over the entire length of the mitral coaptation line. The coaptation of the leaflets depends on the adequate anatomy (integrity of the structures) and adequate functioning of 5 components, which are 1. the mitral annulus, 2. the anterior and posterior leaflets, 3. the mitral chordae, 4. the papillary muscles (PPM) and 5. the ventricular walls themselves.

Any congenital malformation or acquired lesion of one or more of these components can lead to a mitral insufficiency, also known and referred to as mitral regurgitation (MR). As commonly used, mitral insufficiency and/or mitral regurgitation is a result of the mitral valve not hermetically closing during ventricular contraction. As a result, a variable amount of blood leaks back into the LA. This situation correlates with a poor outcome for the patient, since it increases the workload to the heart, as well as it increases the volumes of the left atrial and ventricular chambers.

Furthermore, the existence of severe mitral regurgitation and ventricular dilatation generate a vicious cycle in which MR begets more MR. Indeed when the ventricle increases in size the distance between the papillary muscles increases, tethering the mitral chordae and impeding their full motion up to the plane of the annulus. The native annulus of the mitral valve may also increase. This patho-physiological continuum leads to heart failure, pulmonary hypertension, atrial fibrillation and ultimately death. The treatment of MR includes the administration of pharmacological drugs. However in most cases the regurgitation treated either by surgical repair or replacement of the valve. In some selected cases, an emerging percutaneous technology is used. However, this procedure is still under evaluation and involves the Mitraclip® or other emerging technologies that are currently under development.

Although there is a considerable trend to fix the MR as early as possible in its natural course, the indication and timing of the intervention rely also on the etiology of the condition, as well as on the functional anatomy and structural damage to the valve and the ventricle. One particular case of mitral regurgitation is referred to as structural mitral regurgitation (SMR). This includes a structural deterioration of the mitral valve and is usually the consequence of Barlow's disease or of fibro-elastic degeneration (FED). This condition is extremely prevalent and can be found, according to different studies, in about 2-4% of the adult population.

Repairing structural mitral insufficiency poses particular problems and challenges that have been approached in different ways. Such include a surgical approach through various incisions in the patients' chest using cardiopulmonary bypass (CPB) on the arrested heart. Less frequently the approach involves, percutaneously using an endovascular, catheter that requires, a trans-septal puncture. The trans-septal puncture involves drilling a hole in the inter-atrial septum in order to reach the left atrial chamber of the heart from the punctured vein. This manoeuver requires sophisticated infrastructures and highly trained teams and can be applied only in carefully selected, hence limited, subcategories of patients.

Surgery is currently regarded as the golden standard of treatment to repair the mitral valve and is therefore performed in the vast majority of the cases. When the valve is repaired technical failure is not a rare event as up to 20% of the patients who undergo repair experience recurrence of severe mitral regurgitation during the first post-operative year. In a significant number of cases of SMR, generally less than 50%, the leaking valve is replaced rather than repaired. This occurs for numerous reasons including technical difficulties and insufficient physician's experience/caseload. Replacement represents a loss of chances for the patient as compared to repair with an estimated increase in the mortality risk around 15% at five years after the operation for SMR. In any case open heart surgery remains a major acute insult to patients' physiology with risks of complications arising mainly from three maneuvers: sternal division ("sternotomy"), CPB and aortic clamping/manipulations. Generally such an operation corresponds in terms of bodily inflammatory response to that of a third degree burn of 25% of the body surface area.

Therefore, an alternative solution allowing an easier, less invasive, more reproducible, and possibly safer and more durable reduction or disappearance of the mitral regurgitation is needed to overcome the problems as generally set forth above.

SUMMARY OF THE INVENTION

This invention is directed to the use of an intra-cardiac pre-shaped device, where in one or more preferred embodiments comprise a grid tailored or more specifically corresponding in dimension and configuration to patient's mitral valve anatomy. As such, the intracardiac device of the present invention includes a base having a dimension and configuration which corresponds to that of the native annulus and leaflets of the mitral valve.

More specifically, the device of the present invention comprises a base including a peripheral portion connected in at least partially surrounding relation to a central portion. As indicated, the base and or its components may be pre-formed and structured prior to its application to correspond in both dimension and configuration to the mitral valve including the native annulus thereof. Such preoperative structuring may be in accord with a three-dimensional (3-D) print of the patient's mitral valve. As such, the patient's mitral valve, using any of a plurality of appropriate imaging techniques, may be "reconstructed" in three dimensions, in order to assure an accurate, customized dimensioning and configuring of the base. Such imaging techniques are known in the medical profession and related prior art and may include, but are not limited to, a CT scan, MRI, 3D echo imaging, etc.

The preoperative dimensioning and configuring of the base of the device facilitates its securement in an appropriate operative position relative to the mitral valve being treated. As set forth above, the base comprises a peripheral portion and a central portion secured to the peripheral portion and being surrounded thereby. The central portion comprises a grid or open mesh configuration or other appropriate structure which facilitates the flow of blood through the central portion. Moreover, the grid or open mesh configuration comprises a plurality of openings which are collectively disposed, dimensioned and configured to facilitate the aforementioned normal blood flow there through, from the left atrium to the left ventricle. Such facilitated blood flow is necessary due to the operative positioning of the base in an overlying relation to the mitral valve substantially or at least partially on the interior of the left atrium. As a result, during the normal functioning of the heart, blood will flow through the grid or open mesh of the central portion, through the open orifice of the mitral valve and into the left ventricle, when the heart is in diastole.

In addition, the central portion including the grid or open mesh configuration will also be disposed in overlying, movement restricting relation to at least one of the leaflets of the mitral valve, when the base is in the aforementioned operative position. Therefore at least a part of the central portion will be disposed in engaging relation with at least one of the valve leaflets preferably, but not necessarily exclusively, at an area in overlying alignment with the regurgitating orifice. As used herein, the "regurgitating orifice" is intended to describe the opening between the leaflets of the mitral valve through which blood flows from the left ventricle back into the left atrium during diastole. As explained in greater detail hereinafter, the grid or open mesh configuration may include the aforementioned plurality of openings extending over a predetermined part of the central portion or at least a majority of the central portion. In at least one embodiment, substantially the entirety of the central portion is comprised of the plurality of openings which facilitate the aforementioned blood flow, during an open orientation of the mitral valve, into the left ventricle. As will be explained in greater detail hereinafter, the open mesh construction of the central portion will still provide sufficient resistance to at least one of the leaflets to restrict its movement back into the left atrium. Accordingly, it is emphasized, that the intended structural and operative features of the base, being correspondingly dimensioned and configured with mitral valve being treated, facilitates both blood flow through the mitral valve as well as the restriction of movement or prolapse of at least one valve leaflet. As a result, the device of the present invention, when operatively positioned relative to the mitral valve will restrict or at least decrease the propensity for mitral regurgitation.

As indicated, the base also comprises a peripheral portion which preferably includes an annular configuration and/or ring structure. The ring structure is anchored adjacent to the native annulus of the mitral valve and/or directly thereto such that the grid or open mesh of the central portion is disposed in overlying relation to the valve leaflets of the mitral valve. Further, the material from which the peripheral portion or ring of the base is formed may be accurately described as being flexible and "semi-rigid". As used with regard to the physical characteristics of the ring, the term semi-rigid is meant to include a material having sufficient flexibility facilitate movement of the ring with the native annulus between the normal open and closed orientations of the mitral valve. At the same time, the semi-rigid material as well as the configuration of the stabilizing ring preferably includes sufficient rigidity to restrict or limit an abnormal or undesired dilation or expansion of the native annulus, when the ring is anchored to and/or adjacent the native annulus, while the base is in the operative position. As a result of limiting the dilation or expansion of the native annulus, the size of the mitral orifice will also be limited so as to not expand or dilate beyond a normal size.

An additional structural feature of the intracardiac device includes the ring having a length which is equal to at least a majority and preferably substantially the entirety of the circumference of the native annulus. As such, at least a majority or substantially the entire length of the ring is anchored directly or adjacently along at least a majority or preferably the entirety of the circumference of the native annulus. Also, in order to provide more accurate fitting or attachment of the ring relative to the native annulus, the ring may not have a continuous configuration. More specifically, the ring may include free opposite ends which when in an operative position, are disposed in adjacent but spaced relation to one another.

Structural and operative features of the grid or open mesh of the central portion may include it being formed of a material having sufficient flexibility to move with the mitral valve as it is disposed between the open and closed orientations. However, the central portion should also include sufficient rigidity, strength, tenacity, etc. to restrict movement of at least one of the valve leaflets and prevent prolapse thereof into the left atrium as the mitral valve assumes a closed or orientation during systole. To this end, the central portion, including the open mesh grid may have a substantially "bowed", at least partially "domed" or similar, outwardly projecting configuration. In more specific terms, such a preferred bowed or domed configuration of the central portion facilitates it at least partially entering the orifice of the mitral valve at least when the mitral valve is in an open orientation. However, upon a closing of the mitral valve the bowed configuration may at least minimally retract or otherwise be reoriented such that it remains in engaging and/or movement restricting relation to at least one leaflet of the mitral valve at least during systole in order to prevent the aforementioned prolapse thereof.

Introduction of the device may be accomplished by an introductory catheter passing through the left atrial wall. As at least partially indicated above, the flexibility of both the peripheral portion or ring and the central portion of the base is such as to allow it to be initially disposed in a folded, crimped or other reduced volume orientation. When so oriented within the interior, the base will be disposed within the interior of the introductory catheter to be delivered to the interior of the left atrium. In addition, an additional catheter or positioning instrument may also be disposed on the interior of the introductory catheter in associated relation with the base. Once the introductory catheter is disposed within the interior the left atrium, the positioning instrument forces the device out through an access opening of the introductory catheter. Further, the flexible and/or semi-rigid structuring of the material of the device may also include a sufficient "inherent bias". As such the base will automatically expand into its intended configuration for anchoring and/or placement in the operative position relative to the mitral valve.

As indicated, the central portion is secured to the peripheral portion ring and is surrounded thereby. In turn, when applied in its operative position, the ring is anchored adjacent to or indirect attachment with the natural annulus of the mitral valve. Such anchoring may occur through appropriate suturing or through the utilization of a plurality of anchoring hooks or other appropriate connectors which will securely connect and maintain the peripheral portion ring in the operative position relative to the native annulus.

Additional features relating primarily, but not exclusively to the application of the base to the mitral valve may include a separate attachment or anchoring of both the peripheral portion ring and the central portion. More specifically, the central portion ring can be initially applied into the interior of the left atrium and anchored in its intended location relative to the natural annulus. Thereafter, the central portion may be entered into the left atrium and connected about its periphery to the peripheral portion ring in a secure and reliable manner. In contrast to the above, the central portion and the peripheral portion ring may be connected to one another pre-operatively and prior to introduction into the left atrium.

Therefore, different structural lesions can affect the anatomy of the mitral valve leading to mitral regurgitation. The device of the present invention, as described herein is primarily targeted at fixing "flail" leaflets i.e. leaflets that are "prolapsed" because of chordal rupture and/or extension also overcome and/or restrict mitral regurgitation from other etiologies. More, technically the device of the present invention corresponds to a type II according to Carpentier's classification. It is an extremely frequent phenomenon.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 15 is a detail view in partial cutaway of one preferred embodiment of an interconnection between the stabilizing ring and grid structure as represented in FIG. 14.

FIG. 16A is a schematic view in partial cutaway of a positioning instrument structured to dispose at least the stabilizing ring, of the embodiment of FIG. 12, in an operative orientation relative to the mitral valve.

FIG. 16B is a schematic view in partial cutaway of the positioning instrument of FIG. 16A in a non-inflated state and having the stabilizing ring of the embodiment of FIG. 12 operatively positioned thereon.

FIG. 16C is a schematic plan view of the positioning instrument of the embodiment of FIGS. 16A-16B be in a fully inflated state with the stabilizing ring disposed in an operative position thereon.

FIG. 17A-17C are transverse schematic sectional views of an insertion of the inflated positioning instrument, of the embodiments of FIGS. 16A-16C inserted in a mitral orifice of the mitral valve and being successively oriented during inflation.

FIG. 19 is a schematic representation of the stabilizing ring being disposed in an operative orientation relative to the mitral valve by the positioning instrument.

Like reference numerals refer to like parts throughout the several views of the drawings.

DETAILED DESCRIPTION OF THE PREFERRED EMBODIMENT

Figure 1:
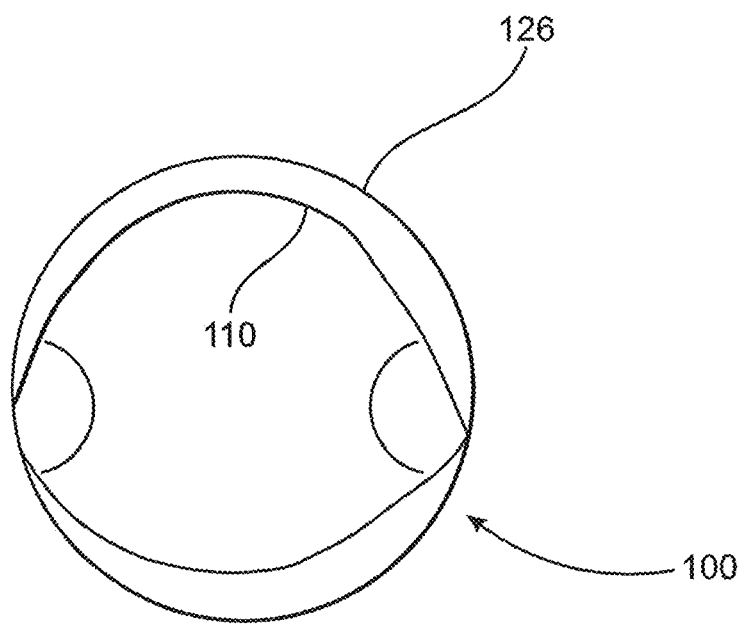
FIG. 1 is a schematic representation of an open orientation of the mitral valve orifice.
Figure 2:
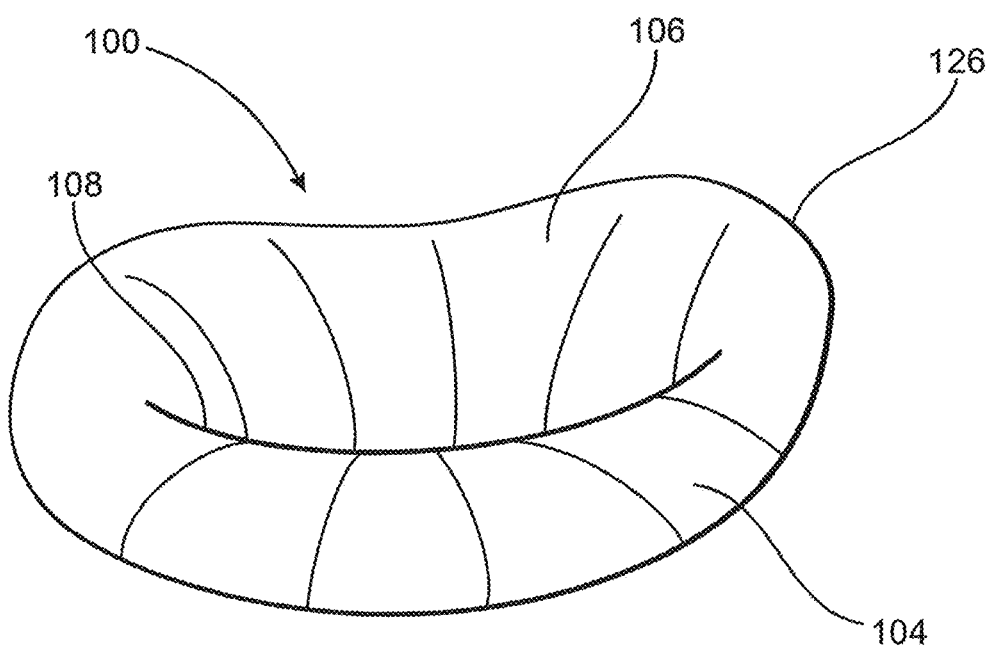
FIG. 2 is a schematic representation of a closed orientation of the mitral valve orifice.
Figure 3:
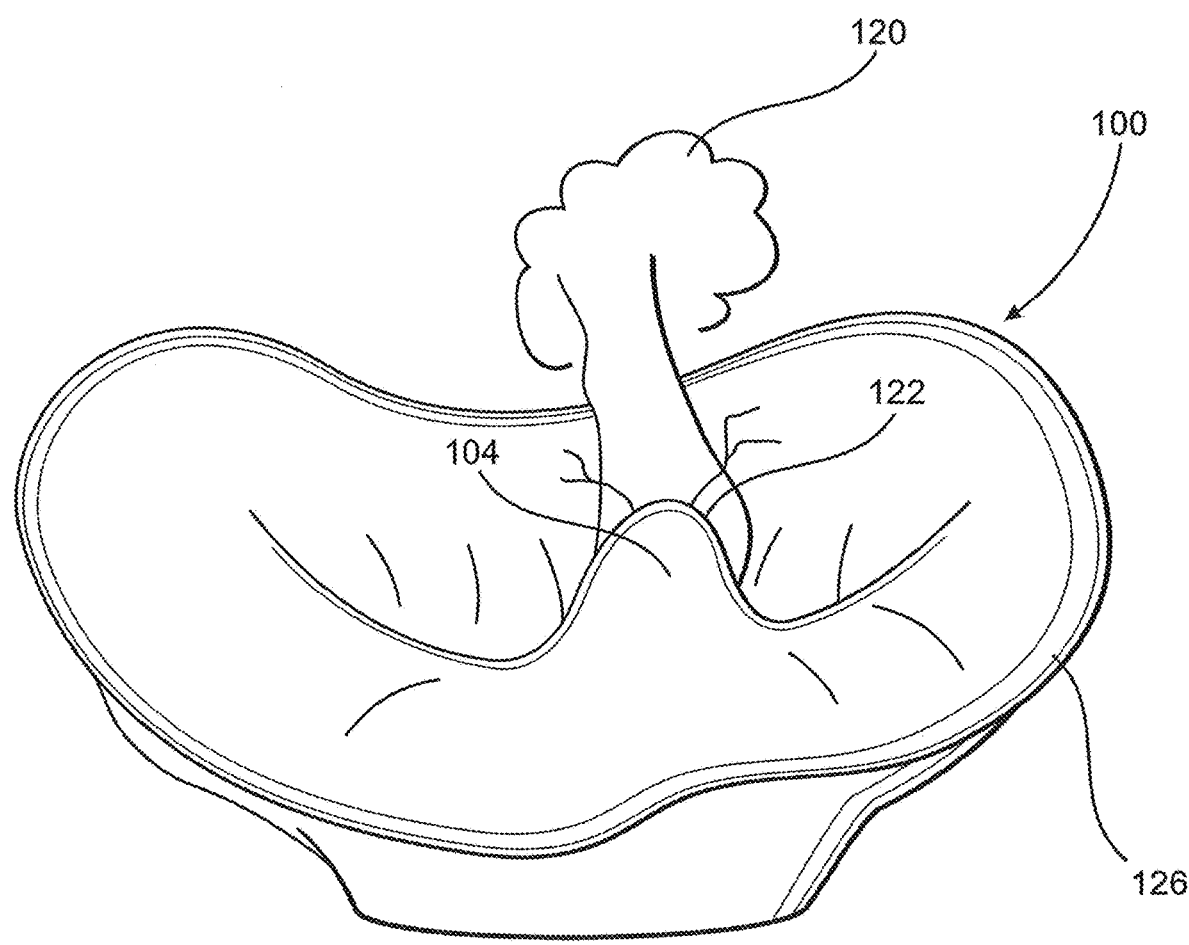
FIG. 3 is a perspective view in schematic form of a leaflet of the mitral valve in prolapse further demonstrating mitral regurgitation.

As represented in the accompanying FIGS. 1-11, the present invention is directed to an intracardiac device, generally indicated as 10, which is structured to restrict prolapse of a mitral valve leaflet, as at 104, and by doing so restrict or diminish mitral valve regurgitation, as schematically represented in FIG. 3. More specifically, the base 12 includes an outer peripheral portion 14 having a substantially annular configuration. As such the peripheral portion 14 may include a ring structure. As also represented the central portion 16 is connected along its outer circumference to the peripheral portion 14 so as to be substantially or at least partially surrounded thereby, as clearly represented in the Figures. As also represented, the peripheral portion ring may not be continuous. More specifically, in order to facilitate the disposition of the ring 14 in the preferred operative position, the opposite ends may be disposed in adjacent but spaced relation to one another when in the operative position, relative to the natural annulus 126.

Further, the central portion 16 of the base 12 comprises a grid construction or configuration which is more specifically defined as an open mesh construction or configuration. As such, the grid or open mesh of the central portion 16 comprises a plurality of openings cooperatively disposed, dimensioned and configured to facilitate the passage of fluid, specifically including blood, there through, as will be explained in greater detail hereinafter with primary reference to FIG. 5.

While the general configuration of the peripheral ring portion 14 is represented in the Figures, the base 12 and its components may be formed and/or structured preoperatively so as to correspond in both dimension and configuration to the mitral valve 100, including the native annulus 102 thereof, to which it is applied. Such preoperative structuring may be in accord with a three-dimensional (3-D) replica of the patient's mitral valve 100. As such, required dimensions and/or configuration of the patient's mitral valve 100 may be determined using a variety of scanning techniques known in the medical profession and related arts. Moreover, the generally customized dimensioning and configuration of the base 12 of the device 10 facilitate its securement in an intended operative position relative to the mitral valve 100 being treated.

In the normal functioning of the heart, the mitral valve 100 will repetitively move between an open orientation (diastole), as represented in FIG. 1, and a closed orientation (systole), as represented in FIG. 2. As such, when in a closed orientation the valve leaflets 104 and 106 close along a coaptation line 108. In contrast, when in an open orientation the natural mitral orifice 110 of the mitral valve 100 is open to facilitate blood flow there through from the left atrium to the left ventricle during diastole of the heart. Accordingly, the plurality of openings of the grid or open mesh which at least partially define the central portion 16 may extend across substantially the entirety thereof or at least along a major portion thereof. However, the collective disposition of the plurality of openings must be such as to assure adequate blood flow through the mitral valve 100 from the left atrium to the left ventricle. It is also noted that certain segments or parts of the open mesh of the central portion 16 may be structured to include a greater density. Such increased density may be defined by the plurality of openings in the dense segment greater in number and more closely positioned. This increased density may further facilitate the movement restricting engagement or relation of the central portion 16 relative to one or more of the valve leaflets 104 or 106.

Figure 4:
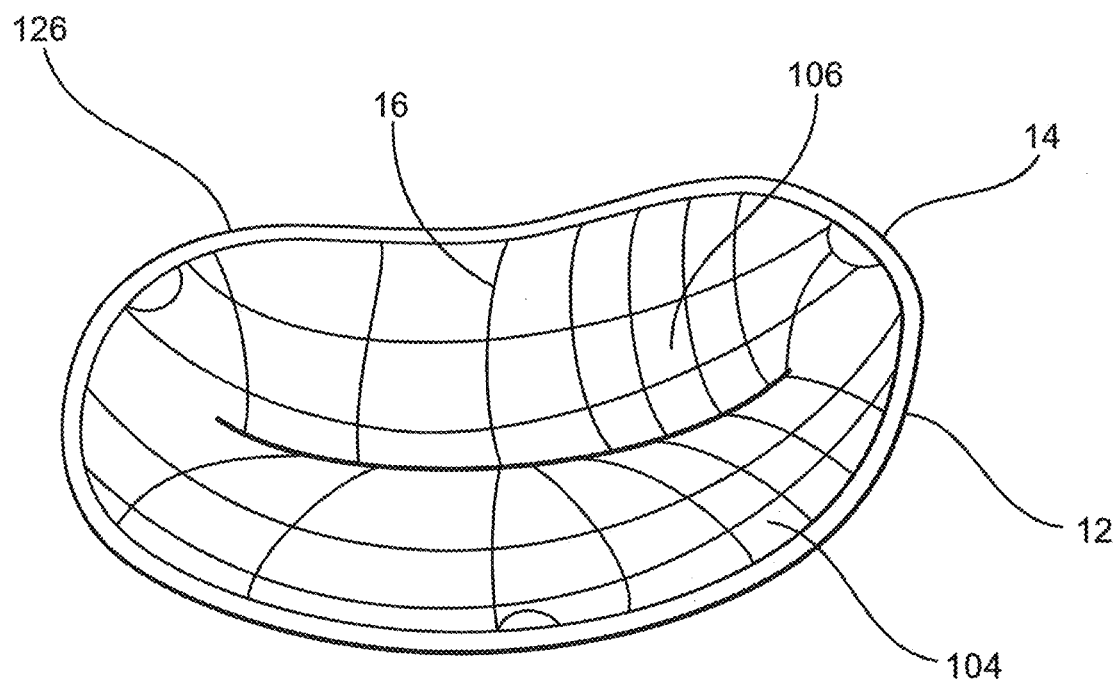
FIG. 4 is a perspective view in schematic form of the device of the embodiment the device in an operative position overlying the leaflets of the mitral valve.
Figure 5:
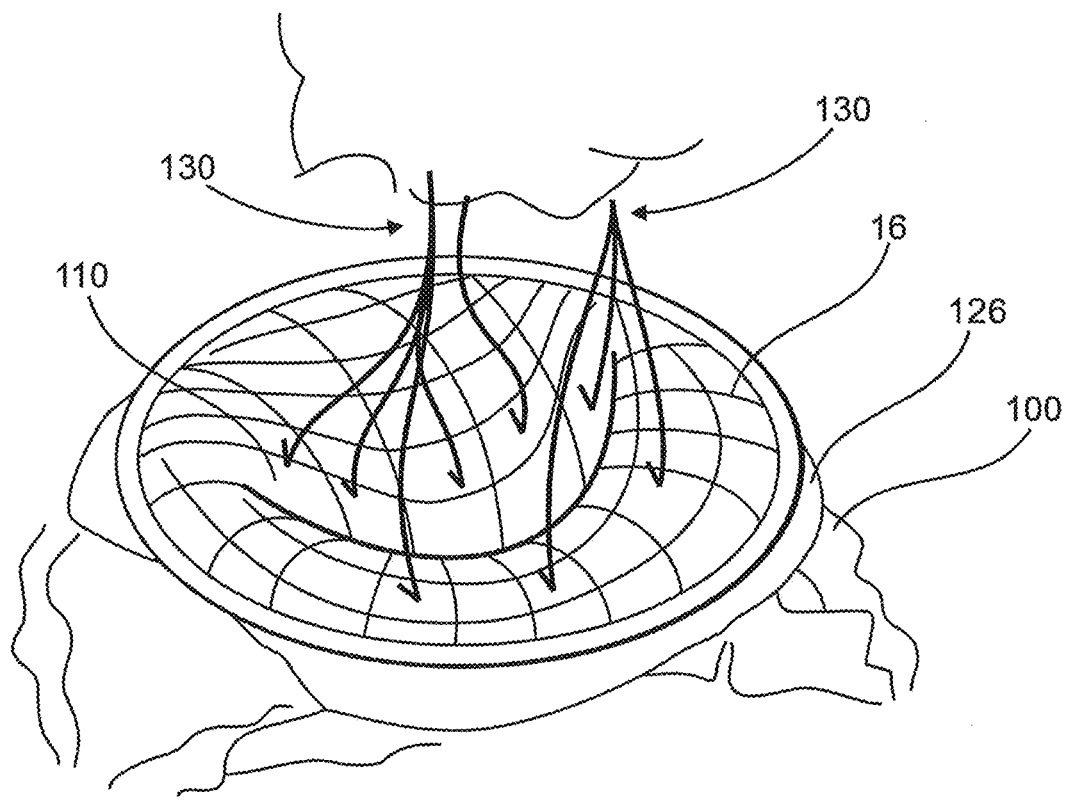
FIG. 5 is a perspective view in schematic form of normal blood flow from the left atrium through the mitral valve, where in the device of the embodiment of FIGS. 1 and 4 are in an operative position.
Figure 6:
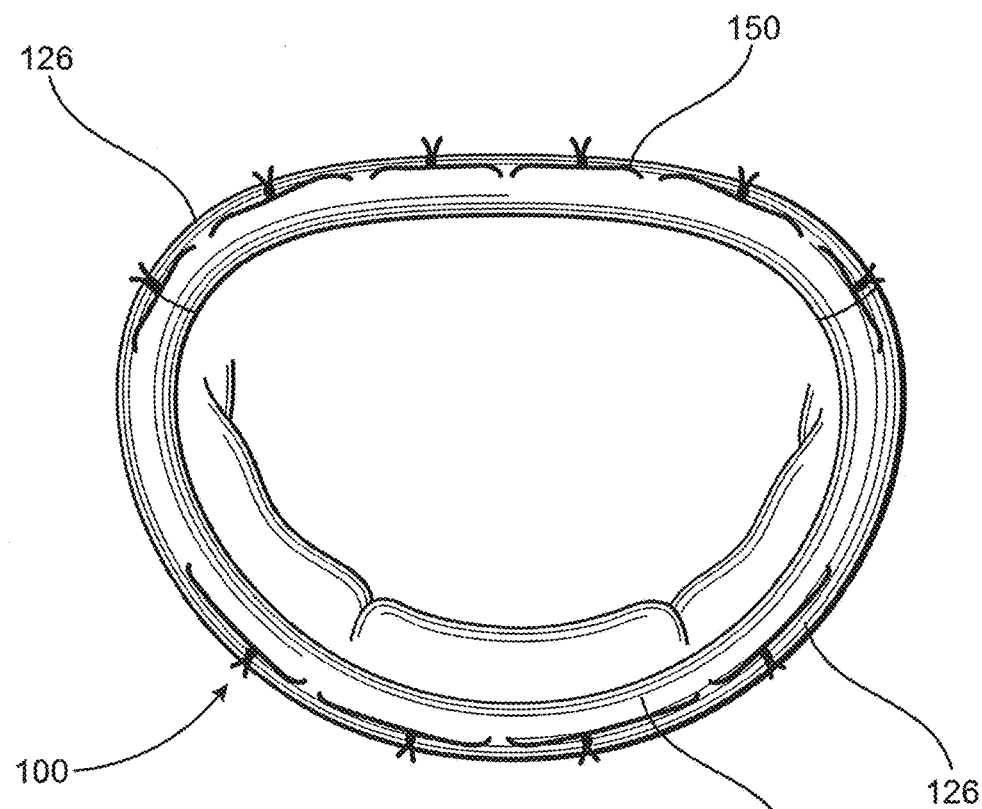
FIG. 6 is a perspective view in schematic form of the peripheral portion of the base of the embodiment of FIGS. 3-5 secured in an operative position to the native annulus of the mitral valve.

As indicated and with reference to FIGS. 3-5, the device 10, including the base 12, is disposed in an operative position so as to restrict movement of at least one of the valve leaflets 104 and 106. In restricting movement or prolapse of a corresponding leaflet, mitral regurgitation, as schematically represented FIG. 3, may be eliminated or reduced. As represented a leaflet 104 of the mitral valve 100 is in a state of prolapse as it moves back into the left atrium. As a result, mitral regurgitation occurs allowing a flow of blood 120 back into the left atrium through a regurgitation orifice 122. Therefore, the preferred operative position of the base 12 is schematically represented in FIGS. 4 and 6. As such, the peripheral portion or ring 14 is secured adjacent or directly to the natural annulus 126 of the mitral valve 100. In such an operative position the central portion 16, including the grid or open mesh, is disposed in overlying relation to one or both of the mitral valve leaflets 104 and 106. Further, the base 12 will remain connected in its operative position when the mitral valve 100 is in the closed position of FIG. 4 as well as the open position of FIG. 5. The overlying disposition and movement restricting engagement of the open mesh of the central portion 16 will also remain in movement restricting engagement with the one or more valve leaflets 104 and 106 during both the closed an open orientation of the mitral valve 100. As schematically demonstrated in FIG. 5, when in the open orientation (also see FIG. 1), the plurality of openings which at least partially define the central portion 16 facilitates blood flow generally indicated as 130 from the left atrium, through the open mesh and/or grid of the central portion 16 and through the natural mitral orifice 110 of the mitral valve 100.

Figure 7:
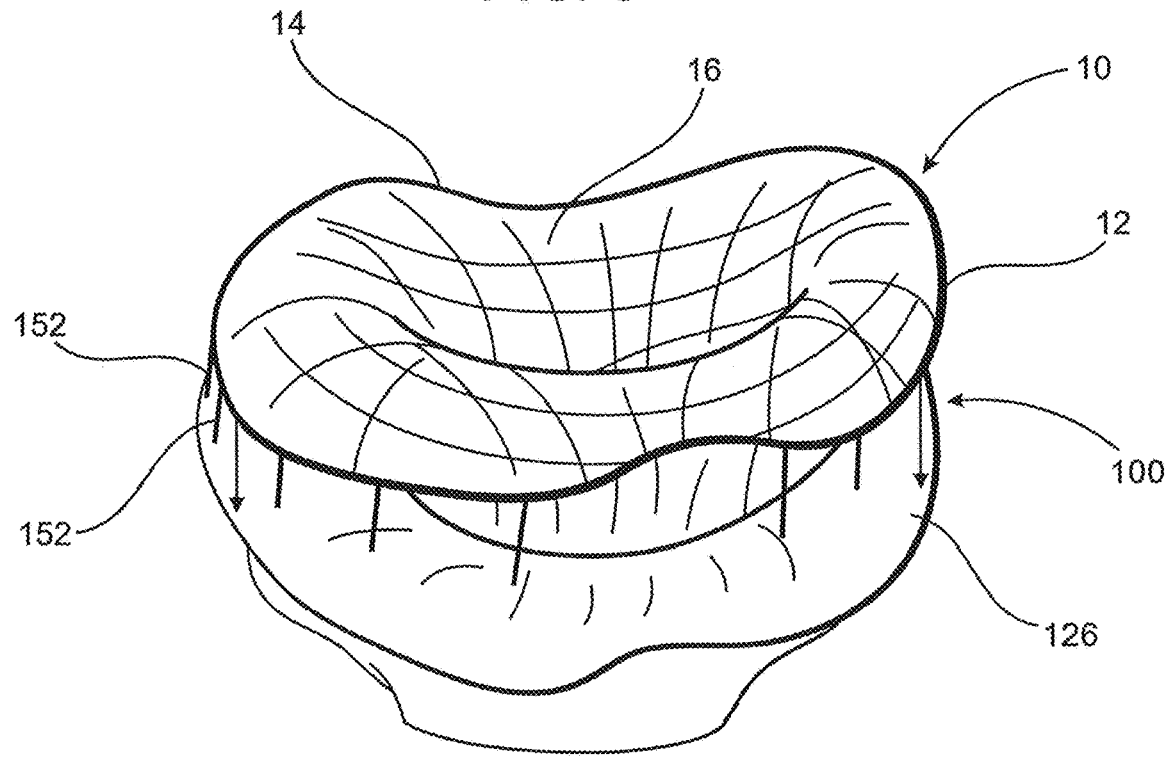
FIG. 7 is a perspective view in schematic form of the device of the embodiment of FIGS. 1-4 in a position for attachment in to the mitral valve using a plurality of connectors.
Figure 8:
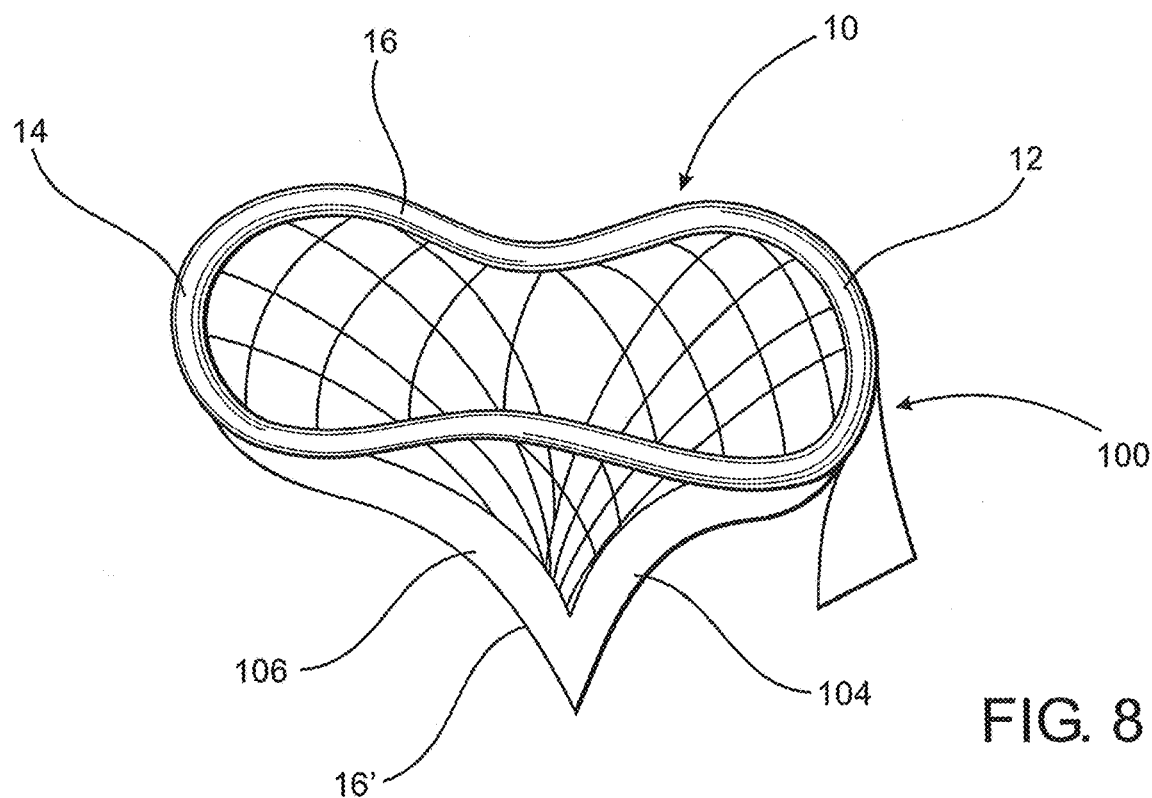
FIG. 8 is a perspective view of the device of FIGS. 1-7 disposed in an operative position relative to the mitral valve leaflets when in a closed orientation.
Figure 9:
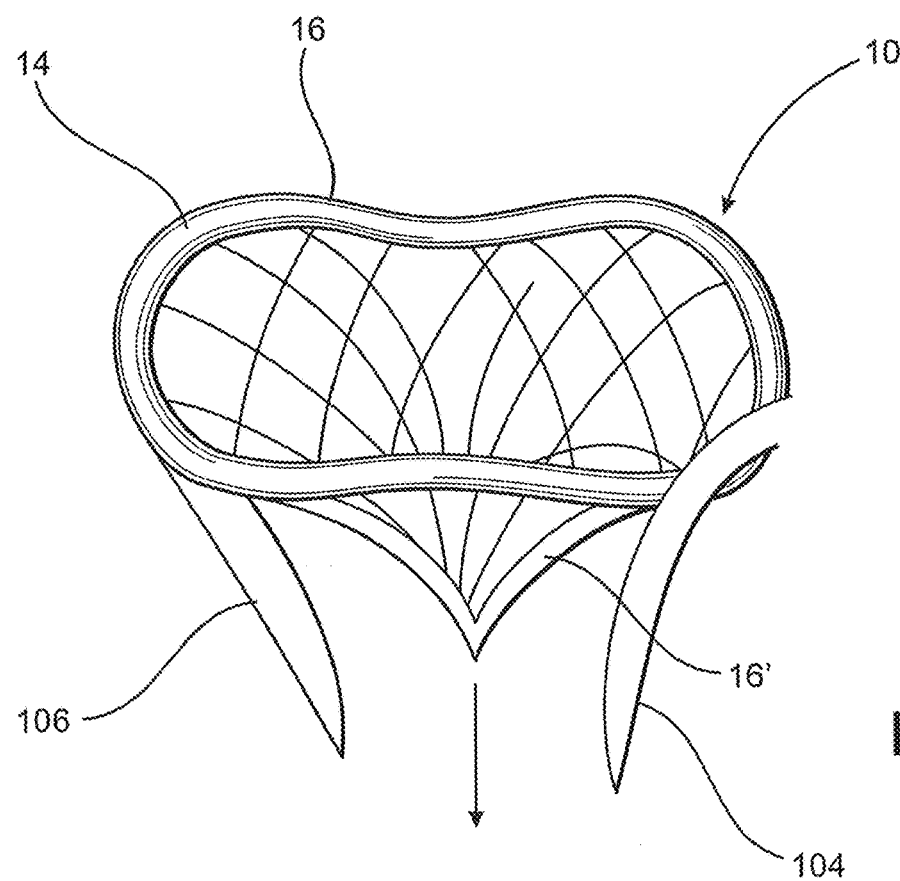
FIG. 9 is a perspective view of the device of FIGS. 1-7 disposed in an operative position relative to the mitral valve orifice, when in an open orientation.

As schematically represented in FIGS. 6 and 7, attachment of the peripheral portion or ring 14 adjacent or directly to the natural annulus 126 may be accomplished by suturing as at 150. In the alternative, a plurality of hook like connectors or other appropriately structured connectors or attachment structures 152 may be affixed to the peripheral portion 14 in spaced relation to one another. As applied, the plurality of connectors will be secured directly to the natural annulus 126 or in a sufficiently adjacent location to dispose the peripheral portion 14 in the manner demonstrated in FIGS. 7 and 8. Therefore, when properly attached to the mitral valve 100 in the operative position, the base 12 will have both sufficient flexibility and rigidity to move with the mitral valve 100, including the natural annulus 126, between the open and closed orientations as represented in FIGS. 1 and 2.

In more specific terms, the material from which the ring 14 is formed may be accurately described as being flexible and "semi-rigid". As used herein, this term with specific regard to the peripheral portion ring 14 is meant to include a material having both a degree of flexibility and a degree of rigidity. Moreover, the material of the peripheral portion ring 14 is sufficiently flexible to facilitate movement of the ring 14 with the native annulus 126 between the open and closed orientations of the mitral orifice 110 of the mitral valve 100, as it passes between the diastole and systole phases of the heart cycle. At the same time, the semi-rigid material of the stabilizing ring 12 preferably includes a sufficient rigidity to restrict or limit a predetermined and/or abnormal dilation or expansion of the native annulus 126 and the mitral orifice 110, upon movement of the natural orifice 110 into the open orientation during diastole, when the ring 14 is anchored to or adjacent the native annulus 126, as represented throughout the FIGS. 1-11.

In turn, limiting or preventing the abnormal expansion of the natural annulus 126 prevents an abnormal dilation or expansion of the mitral orifice 110 during the diastole phase of the heart cycle. It is recognized that abnormal or unusual expansion, dilation, etc. of the mitral orifice 126 may result in prolapse of one or more of the mitral valve leaflets. Accordingly, in situations where weaker dictation of the mitral valve 100 is an occurrence, restricting abnormal expansion of the natural annulus 126 will in turn restrict and abnormal enlargement, dilation or expansion of the mitral orifice 110.

For purposes of clarity, during the diastole phase, the natural orifice area is normally 7.1 (plus or minus) 1.3 cm$^2$. Accordingly the stabilizing ring 14 is structured through its predetermined dimension and configuration, corresponding to the natural annulus 126, as well as the flexible, semi-rigid material from which it is formed, to restrict dilation or expansion of the natural annulus and accordingly restrict dilation or expansion of the natural orifice 110 beyond the 7.1+1.3 cm$^2$ or 8.4 cm$^2$ maximum normal size.

Somewhat similarly, the structural and operative features of the grid or open mesh of this central portion 16 includes a sufficient amount of rigidity, strength and integrity to restrict movement of at least one of the valve leaflets 104 and 106. Such restricted movement prevents or reduces prolapse of the one or more leaflets 104 and 106 as the mitral valve 100 assumes a closed orientation during systole. At the same time, the grid or open mesh of the central portion 16 should have sufficient flexibility to accommodate and move with the different orientations of the mitral valve 100 including the natural orifice 110 and the native annulus 126. Therefore, with primary reference to FIGS. 7-9, the grid or open mesh of the central portion 16 may include a substantially "bowed" or "domed" configuration generally indicated as 16'. As such, the bowed configuration 16' is disposed, dimensioned and configured to extend outwardly from the left atrium and the ring 14 to which is attached and be disposed in movement restricting engagement with one or both of the leaflets 104 and 106 of the mitral valve 100 when in the closed orientation of FIG. 7. Also, the substantially bowed or domed configuration 16', as well as the flexibility of the central portion 16, will facilitate at least a partial insertion or passage of the bowed segment 16' from the left atrium through or into the natural orifice 110 of the mitral valve 100 when the mitral valve 100 is in the open orientation (diastole) of FIG. 9.

Figure 10:
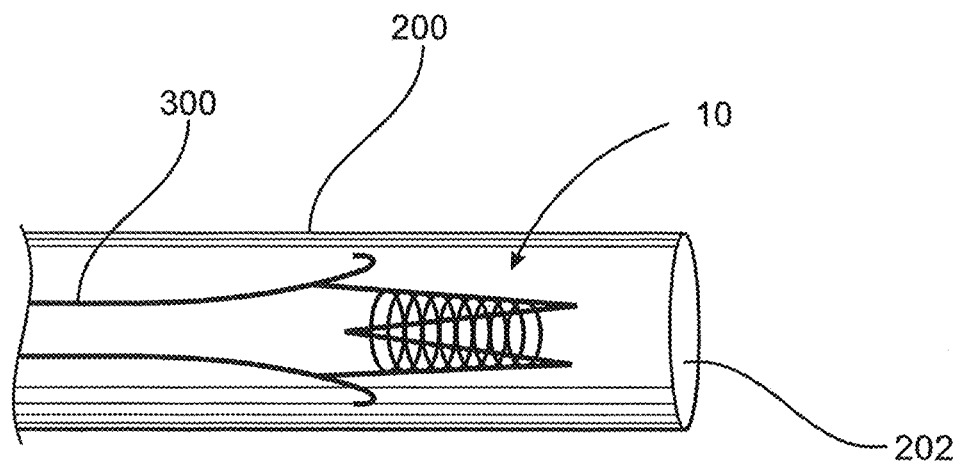
FIG. 10 is a perspective view in schematic form of one method and/or procedure for inserting the device of the present invention into the left atrium in preparation for attachment to the mitral valve in an operative position.
Figure 11:
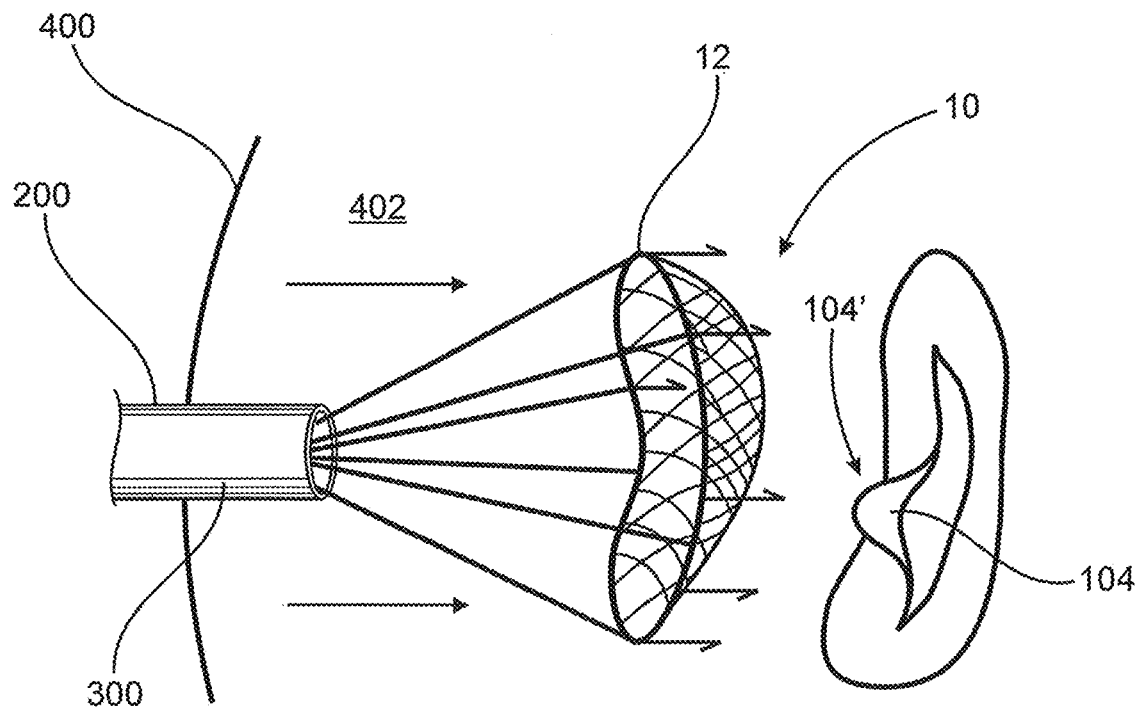
FIG. 11 is a perspective view in schematic form of the embodiment of FIG. 10 wherein the device has exited an introductory catheter and is disposed in position for attachment to the mitral valve.
Figure 12:
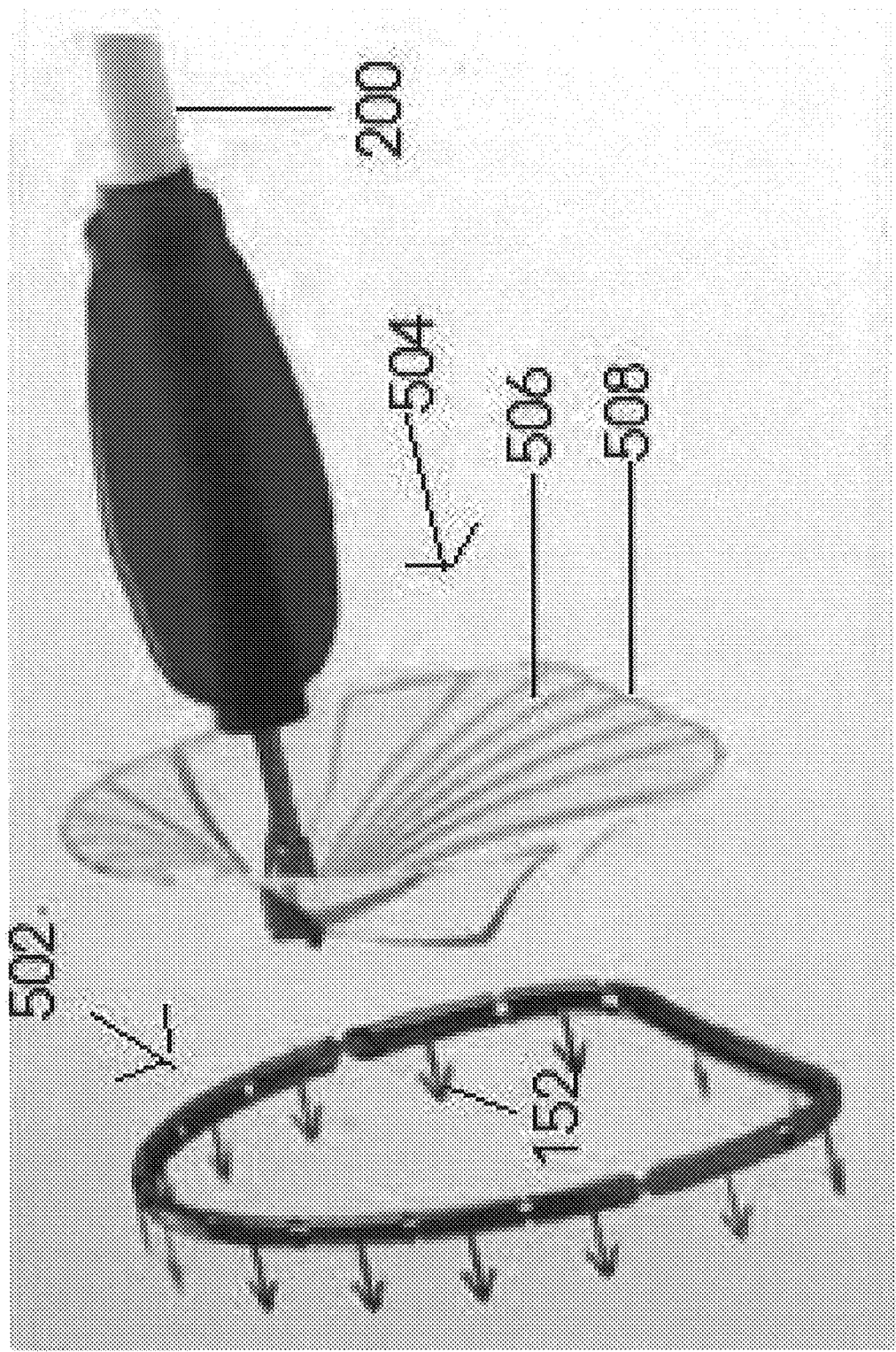
FIG. 12 is a schematic view in exploded form of another preferred embodiment of the present invention comprising an assembly structured to restrict regurgitation of a mitral valve.

With primary reference to FIGS. 10 and 11, introduction of the device 10 may be by and introductory catheter 200 passing through a wall 400 of the left atrium 402. As generally indicated above, the flexibility and overall structuring of the device 10 allows it to be folded or otherwise manipulated into a reduced volume orientation of sufficiently reduced size to be disposed and moved within the interior of the introductory catheter 200. Also, a positioning instrument 300 may also be operatively disposed within the interior of the introductory or positioning instrument or catheter 200 in direct association with the device 10. Further manipulation of the positioning instrument 300 will cause the device 10 to pass through and out of an access opening 202 once the introductory catheter 200 passes through the atrium wall 400 into the interior of the left atrium 402. Accordingly, as represented in FIG. 12, additional manipulation of the positioning instrument 300 will result in a forced removal of the device 10 from the introductory catheter 200. As also indicated above, the flexibility and other physical characteristics of the material from which the components of the base 12 are formed may also be such as to include an inherent bias. As a result, once the device 10 exits the access opening 202 it will assume its normal expanded orientation, as represented. Once in the normal or expanded orientation the device 10 and base 12 will be disposed relative to the mitral valve 100 for attachment thereto in the aforementioned operative position. For purposes of clarity, the FIG. 12 also represents the mitral valve 100 having at least one leaflet 104 being disposed in prolapse as at 104'.

Additional features relating primarily, but not exclusively, to the insertion and attachment of the base 12 to the mitral valve 100 may include a separate attachment of the peripheral portion ring 14 and a separate or subsequent attachment of the central portion 16. In contrast, the central portion 16 and the peripheral portion ring 14 may be connected to one another preoperatively and prior to disposition of the devise 10 into the introductory catheter 200, as described above.

Yet another preferred embodiment of the present invention is represented in FIGS. 12-19 and is directed to an assembly and method for restricting regurgitation of a mitral valve 100. This preferred embodiment as represented in FIGS. 12-20 is similar in purpose and function but distinguishable in structure and as well as the method of securing the components of the assembly of the additional preferred embodiment, in an operative orientation relative to the mitral valve 100.

Figure 13:
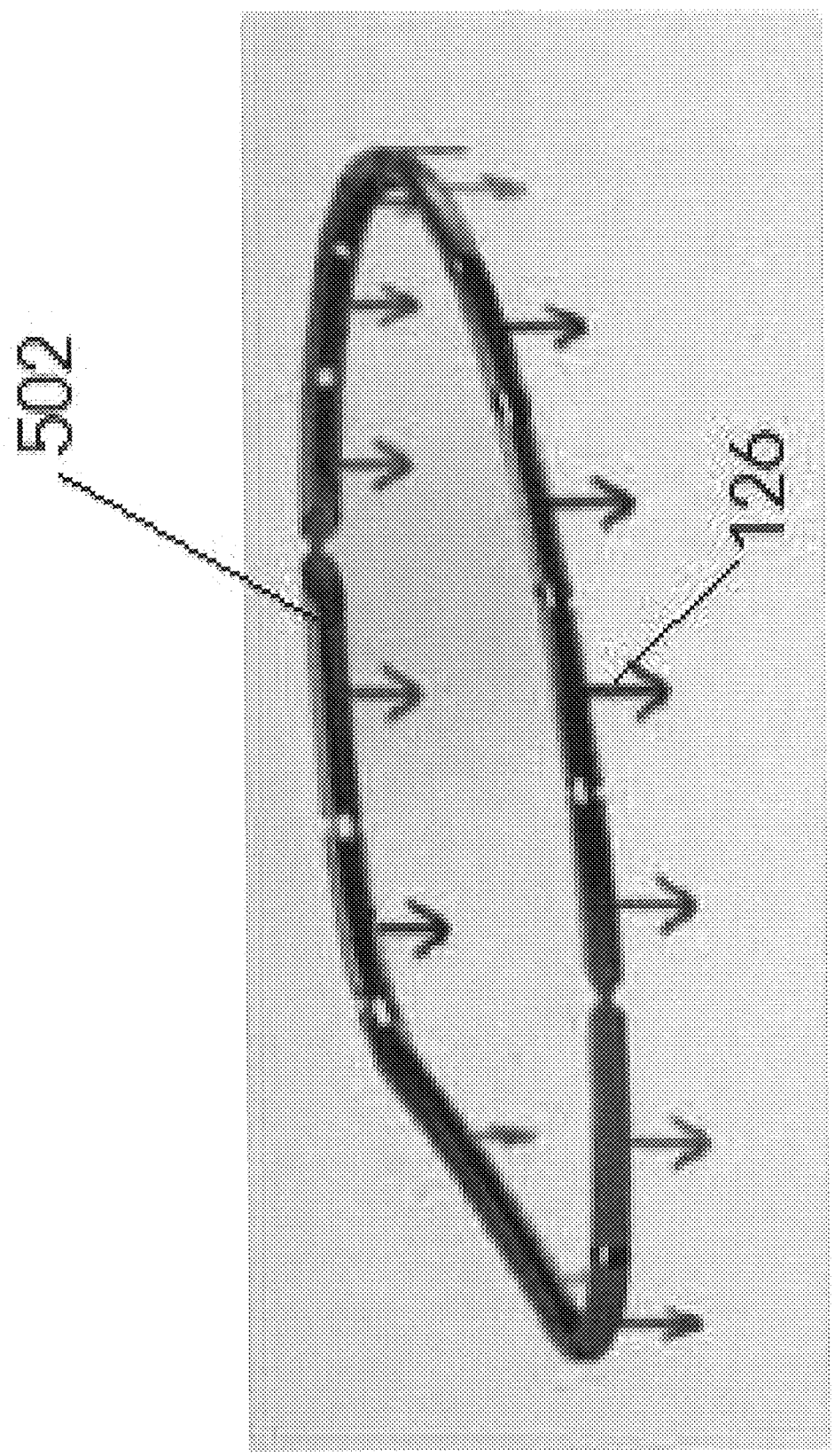
FIG. 13 is a perspective schematic view representing a stabilizing ring associated with the additional preferred embodiment of FIG. 12.
Figure 14:
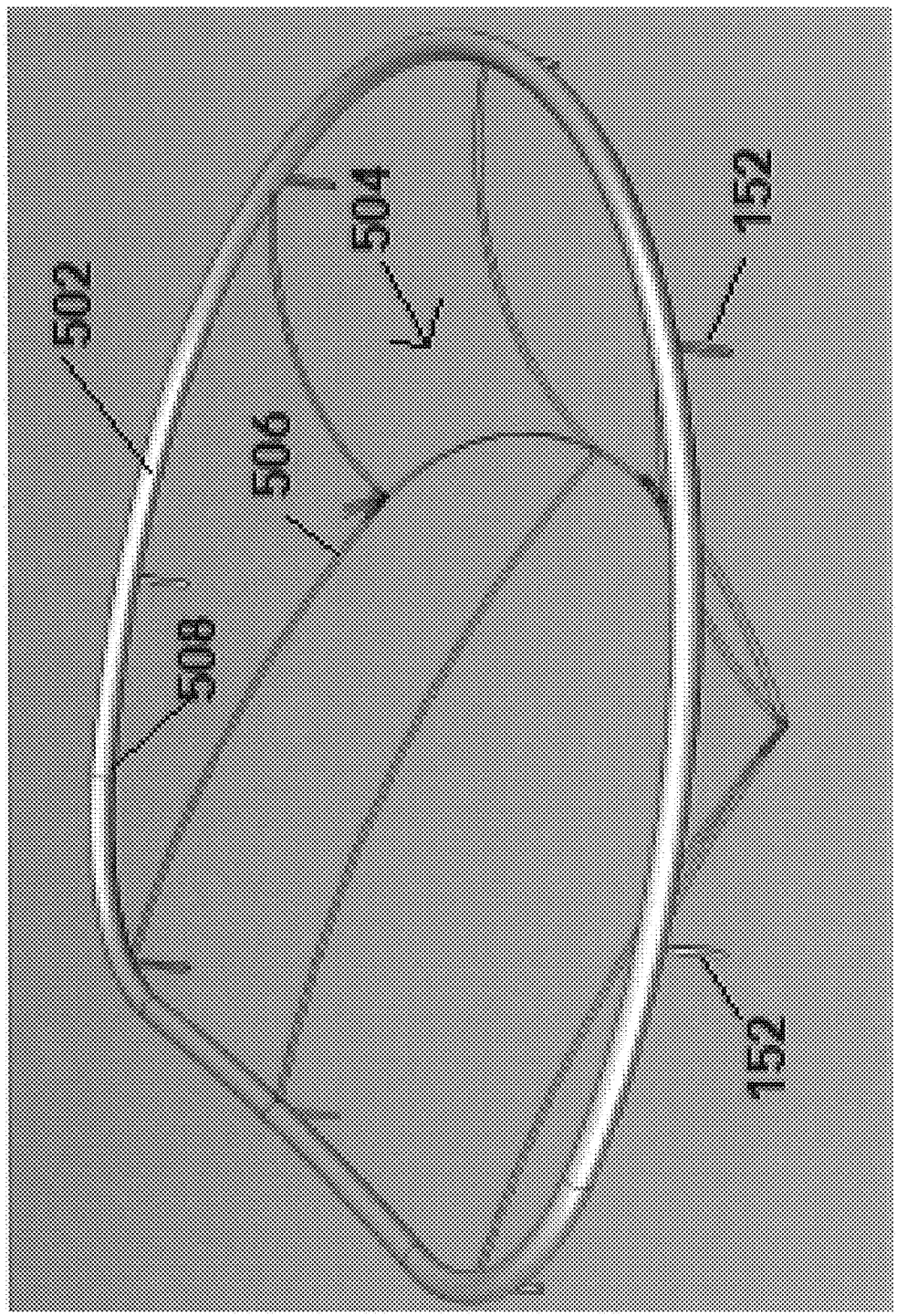
FIG. 14 is a perspective view in schematic form of an assembled stabilizing ring and grid, of the additional preferred embodiment of FIGS. 12-13, not yet independently positioned in an operative orientation relative to the mitral valve.

With initial and primary reference to FIGS. 12-14, assembly of this embodiment includes a stabilizing ring, generally indicated as 502 including, in at least one preferred embodiment, a continuous, closed configuration. Further as with the embodiment of FIG. 7 the stabilizing ring 502 includes an attachment structure comprising at least one but preferably a plurality of connecting or attaching hooks 152 disposed and configured to penetrate into the natural annulus 126, thereby at least partially defining an operative orientation of the stabilizing ring 502.

As also represented in FIG. 12 the assembly of this embodiment comprises a grid generally indicated as 504 having a central portion 506 and an outer peripheral portion 508. As also indicated the central portion 506 includes an outwardly bowed section or portion which, as explained in greater detail hereinafter, will be disposed in movement restricting relation to one or both of the mitral valve leaflets, at least during the systole phase of the heart cycle, as described above in the embodiment of FIGS. 1-11 and in particular as represented in FIG. 4-7.

It is further emphasized that one structural and operative difference between the embodiment of FIGS. 12-20 and that represented in FIGS. 1-11 is the initial and original separation of the stabilizing ring 502 from the grid 504 thereby providing additional versatility to the assembly of this embodiment. Such independent structuring and independent operative orientation facilitates a method and procedure of disposing both the stabilizing ring 502 and the grid 504 in an intended operative orientation relative to the mitral valve 100.

For purposes of clarity, FIG. 14 represents an assembled and/or interconnected stabilizing ring 502 with the grid 504 prior to disposition of the stabilizing ring 502 being initially connected to the natural annulus 126 and the subsequent connection of the grid 504 being independently connected to the ring 502, so as to be interconnected to the mitral valve 100. However, it is again emphasized that the method of defining the components of the assembly being disposed in the "operative orientation" includes the stabilizing ring 502 being initially connected to the natural annulus 126 in at least partially surrounding relation to a mitral orifice 110 and a subsequent introduction of the grid 504 to the mitral valve 100 by being connected to the stabilizing ring 502.

Also for purposes of clarity, FIG. 15 is representative of one structural embodiment facilitating the attachment of the outer peripheral portion 508 of the grid 504 to the ring 502. In this embodiment the ring 502 may include an elongated channel 510 extending along an inner periphery of the ring 502. As such, the outer peripheral portion 508 of the grid 504 may be fitted therein to facilitate a connection of the grid 504 in the intended operative orientation to the ring 502 and interconnected to the natural annulus 126. It is emphasized that the interconnection between the ring 502 and the grid to 504 is provided by example only. Other interconnecting structures and procedures may be utilized to interconnect the grid 504 to the ring 502 in the intended operative orientation, subsequent to the ring 502 being connected to the natural annulus 126 of the mitral valve 100.

It should also be noted that the grid 504 may have different structural configurations wherein the central portion 506 has a liquid permeable, open mesh structure which may differ as made evident from a comparison of the FIGS. 12 and 14. However common to each structural embodiment is the central portion 506 having an outwardly bowed configuration. Also, with regard to the structural details of the stabilizing ring 502, one embodiment is represented as having a continuous, close configuration. Further, the stabilizing ring 502 is structured to conform in dimension and configuration to the natural annulus, specifically, but not exclusively when the natural annulus is in an open orientation (diastole).

It is recognized that the normal diameter of the mitral annulus is 2.7-3.5 cm wherein the circumference is 8-9 cm. However microscopically, there is no clear evidence of a true annular configuration of the mitral annulus located anteriorly, where the mitral valve leaflet is contiguous with the posterior aortic root. Therefore, the stabilizing ring 502 may have a closed, continuous configuration and still maintain its intended operative features in an efficient and effective manner. In contrast, another embodiment of the stabilizing ring 502 may have a substantially non-continuous configuration generally in the form of a C-shape or configuration. In the latter C-configuration the stabilizing ring 502 may be connected along at least a majority or the entirety of the circumference of the normal annulus. Further, the spacing between spaced apart free ends of the substantially C-configured ring 502 may be disposed adjacent and/or aligned with the anterior of the natural annulus, where the corresponding mitral valve leaflet is contiguous to the posterior aortic root, as set forth above.

Further structural and operative features of the ring 502 includes the dimensioning and at least partial configuring thereof to correspond to the natural annulus of the 126 such as when the natural annulus 126 is in an open orientation. Accordingly, the above noted dimensional characteristics of the natural annulus 126 will be incorporated in the ring 502. Moreover, and as set forth above regarding the structural and operative characteristics of the stabilizing ring 12 of the embodiment of FIGS. 1-11, the stabilizing ring 502 is similarly structured. In more specific terms, the ring 502 is formed from an at least partially flexible, semirigid material. As such the flexible, semi-rigid material as well as the corresponding dimensions and configurations of the ring 502, substantially corresponding to the natural annulus 126, facilitates movement of the ring 502 with the natural annulus 126 between open and closed orientations during diastole and systole phases of the heart cycle. However, the indicated configuration as well as the noted structural, material and dimensional characteristics of the ring 502, prevents an "abnormal" or excessive dilation or expansion of the natural annulus 126, which in turn prevents or restricts an abnormal expansion or dilation of the mitral orifice 110, during the diastole phase of the heart. As a result, such "expansion restrictive limits" of the natural annulus 126 and corresponding limits on the abnormal expansion or dilation of the mitral orifice 110, eliminates or significantly restricts the occurrence of prolapse of the leaflets and a resulting regurgitation of the mitral valve 100.

Again for purposes of clarity, during the diastole phase, the dimensional area of the natural orifice 110 is normally 7.1 (plus or minus) 1.3 $cm^2$. Accordingly the stabilizing ring 502 is structured through its predetermined dimension and configuration corresponding to the natural annulus 126, as well as the flexible, semi-rigid material from which it is formed, to restrict dilation or expansion of the natural annulus 126 and accordingly restrict dilation or expansion of the natural orifice 110 beyond the 7.1+1.3 $cm^2$ or 8.4 $cm^2$ maximum normal size.

With primary reference to FIGS. 16A-16C a positioning or introductory instrument is at least partially defined by a catheter 200'. However, the catheter 200' differs from the introductory catheter 200 as represented in FIG. 11 at least to the extent of including an inflatable bladder or balloon generally indicated as 520. Inflation conduits or lines may be integrated in the catheter 200' and be connected to a remote source of pressurized air, fluid, etc. Further, the inflatable bladder or balloon 520 includes a distal segment 522 and a proximal segment 524. When in its inflated state, as represented in FIG. 16C the distal segment 522 includes a lesser diameter or transverse dimension than that of the proximal segment 524. In addition a junction 526 serves to provide a demarcation as well as an interconnection between the distal segment 522 and the proximal segment 524.

With reference to FIGS. 16B and 16C, the stabilizing ring 502 is placed in an "operative position" on the bladder 520 in alignment or immediately adjacent to the junction 526. This operative position of the ring 502, during an inflated state of the bladder 520 serves to dispose the ring 502 in a position to accomplish the operative orientation of the ring 502 in direct connection to the natural annulus 126 as explained in greater detail hereinafter.

For purposes of clarity it is emphasized that the term "operative position" or its equivalent is meant to describe the position of the stabilizing ring 502 on the inflated bladder 520 at the junction 506. As such the stabilizing ring 502 is "operatively position" to assume its "operative orientation" in connection with the natural annulus 126. Therefore the term "operative position" is meant to describe the position of the ring 502 on the inflated bladder as set forth above and clearly represented in FIG. 16C. The term "operative orientation" is meant to describe the stabilizing ring 502 being connected directly to the natural annulus 126. The term "operative orientation is also meant to include the grid 504 being connected directly to the ring 502 as described above and schematically represented in FIGS. 12 and 15.

Figure 18:
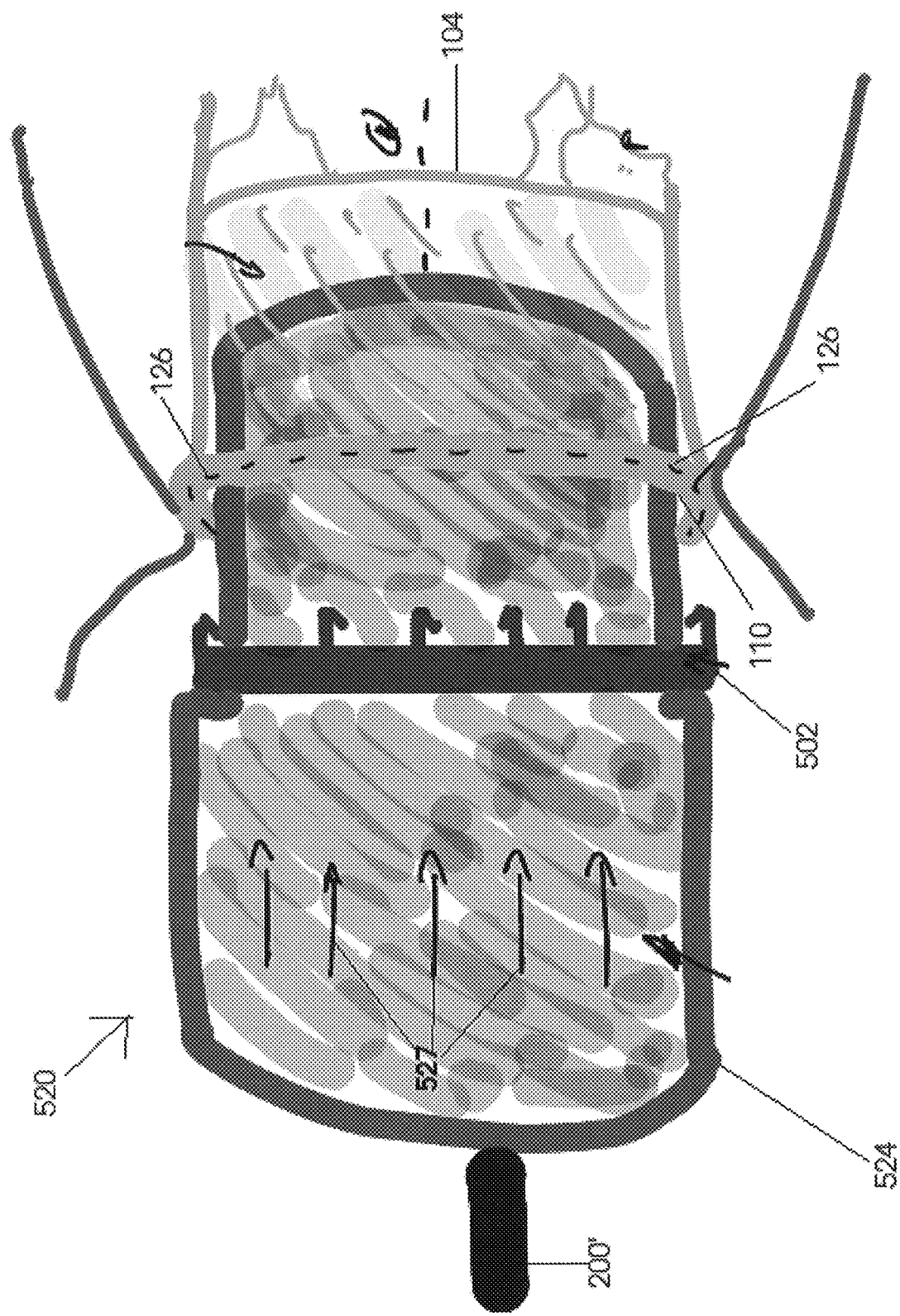
FIG. 18 is a side view of the positioning instrument in an inflated state including a stabilizing ring disposed thereon in an operative position prior to forced disposition of the stabilizing ring in an operative orientation attached to the natural annulus of the mitral valve.

Further, the transverse dimension of the distal segment 522 substantially corresponds to the size of the mitral orifice 110 when in an open orientation, such as during diastole. Therefore the transverse dimension of the distal segment 522 is specifically determined to pass through the mitral orifice 110 in engagement with the outer periphery thereof and may also be sized to at least minimally stretch or expand the outer perimeter of the mitral orifice 110 so as to provide an accurate connection of the ring 502 to the natural annulus 126 in the "operative orientation". As indicated, the proximal section 524 is too large to pass through the mitral orifice 110 and, as represented in FIGS. 18 and 19, the stabilizing ring 502, being located at the junction 526, is disposed in abutting engagement with the corresponding end of the proximal segment 524 of the bladder 520. Therefore when the distal segment 522 is forced through the mitral orifice 110, the stabilizing ring 502 will be forced into penetrating or other appropriate connection with the natural annulus 126. Such a forced connection will be the result of the abutting engagement of the proximal segment 524, when inflated, with the ring 502 concurrent to a force 527, schematically represented in FIG. 18, being exerted on the inflated bladder 520 and the catheter 200'.

As represented in FIG. 17A-17C, the transverse configuration of the distal segment 522 of the bladder 520 is represented as not being circular or around but rather substantially conforming to the overall configuration of the mitral orifice 110 and its inner perimeter 110'. As such, the distal segment 522 of the bladder 520 will effectively assume an automatic alignment and/or conformance as it is extended into the mitral orifice 110. An automatic orientation is schematically represented by directional arrows 600. Further, such automatic orientation may be the result of manipulation of the catheter 200' to which the bladder 520 is attached.

FIG. 19 is a schematic representation of the mitral valve 100 in its natural environment within the left atrium 402. Further, the accurate and definitive placement of the distal segment 522 of the bladder 520 being disposed within the natural orifice 110 is represented. To assure accurate placement, a guide wire may be as at 604 may be secured or anchored to the ventricular wall 606 in spaced relation to the aortic valve 608 and in alignment with a substantial center of the mitral orifice 110, as indicated. When so positioned, the bladder 520 forces the stabilizing ring 502 into its intended "operative orientation" in connection with the natural annulus, such as by penetration of the aforementioned attachment structures 152 into the annulus 126. When so positioned, the distal segment 522 forces the leaflets 104 and 106 into an open or spread orientation.

Therefore, the aforementioned "operative orientation" comprises and may be at least partially defined by the stabilizing ring 502 being connected directly to the natural annulus 126 so as to extend along at least a majority or entirety of its circumference. Also, with reference to FIGS. 12 and 15, the "operative orientation" of the assembly of this embodiment of the present invention also comprises and is at least partially defined by the grid 504 being disposed in connected engagement with the stabilizing ring 502 such that the outwardly bowed portion 506 is disposed in movement restricting engagement with the one or more leaflets 104, 106 of the mitral valve, as also represented in FIGS. 4-6 of the embodiment of FIGS. 1-11. The combination of both the stabilizing ring 502 and the grid 504 being so disposed in the "operative orientation" serves to eliminate or significantly reduce the possibility of the one or more leaflets 104 and 106 of the mitral valve 100 being in prolapse and the concurrent restriction of the possibility of regurgitation of the mitral valve.

With further reference to FIG. 12 the catheter 200 used for operative positioning of the grid 504 may differ from the catheter 200' by not including the inflatable bladder 520. More specifically, the catheter 200 and the operative features of placement of the grid 504 may be substantially equivalent to the representation of grid placement as shown in FIGS. 10-11.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An assembly structured to restrict regurgitation of a mitral valve of the heart, said assembly comprising:
   a ring dimensioned and configured to substantially correspond to a natural annulus of the mitral valve,
   said ring configured to be disposed in an operative orientation on an interior of the left atrium of the heart,
   said operative orientation comprising said ring configured to be connected to and extending along at least a majority of a circumference of the natural annulus,
   a grid comprising a liquid permeable central portion and a circumferential outer portion around a periphery of said central portion, wherein said grid is a separate component from said ring,
   a positioning instrument configured to be removably disposed within the heart and structured to define an operative positioning of at least said ring into said operative orientation, and
   said operative orientation further comprising said circumferential outer portion of said grid connected to said ring, said grid configured to be on an interior of the left atrium, in overlying, movement restricting relation to at least one mitral valve leaflet, at least during a systole phase of the heart cycle.

2. The assembly as recited in claim 1 wherein said ring is formed from an at least partially flexible, semirigid material structured to move with the natural annulus between open and closed orientations of the natural annulus during diastole and systole phases of the heart cycle.

3. The assembly as recited in claim 1 wherein said ring includes a continuous, closed configuration configured to be connected to and extending along substantially an entirety of the natural annulus, when in said operative orientation.

4. The assembly as recited in claim 1 wherein said central portion of said grid comprises a bowed section extending outwardly from said peripheral portion.

5. The assembly as recited in claim 4 wherein said bowed section of said central portion is configured to be disposed in aligned, overlying relation to a coaptation line of the mitral valve leaflets, at least during a systole phase of the heart cycle.

6. The assembly as recited in claim 5 wherein said operative orientation further comprises said bowed section configured to be disposed in movement restricting relation to at least one mitral valve leaflet, during a systole phase of the heart cycle.

7. The assembly as recited in claim 6 wherein said operative orientation further comprises said bowed section configured to be protruding at least partially through a mitral orifice of the mitral valve during the diastole phase of the heart cycle.

8. The assembly as recited in claim 1 wherein said positioning instrument comprises a catheter disposed within the left atrium in communication with the mitral valve, concurrent to said operative positioning of the ring; an inflatable bladder mounted on said catheter, said inflatable bladder disposable in an inflated orientation and a deflated orientation.

9. The assembly as recited in claim 8 wherein said bladder includes a distal segment and a proximal segment connected to one another at a junction; said distal segment including a transverse dimension corresponding to the mitral orifice when open and said proximal segment having a transverse dimension greater than said distal segment and the open mitral orifice.

10. The assembly as recited in claim 9 wherein said operative positioning of said ring comprises said ring disposed in surrounding relation to said distal segment, in aligned relation with said junction and in abutting relation with said proximal segment.

11. The assembly as recited in claim 10 wherein said operative positioning of said ring further comprises said distal segment disposed through the natural orifice and said ring disposed in connecting engagement with the natural annulus.

12. The assembly as recited in claim 11 further comprising said proximal segment forcibly disposed in abutting engagement with said ring concurrent to said ring disposed in said operative orientation connected to the natural annulus.

13. The assembly as recited in claim 12 further comprising an attachment structure mounted on said ring and extending outwardly there from into an attached engagement with the natural annulus; said attached engagement further define said operative orientation.

14. The assembly as recited in claim 1 wherein said ring comprises an elongated channel extending along an inner periphery of the ring to facilitate a connection of the grid to the ring.

* * * * *